United States Patent [19]

Magerlein

[11] 4,448,970

[45] * May 15, 1984

[54] NARGENICIN DERIVATIVES

[75] Inventor: Barney J. Magerlein, Portage, Mich.

[73] Assignee: The Upjohn Company, Kalamazoo, Mich.

[*] Notice: The portion of the term of this patent subsequent to Dec. 14, 1999 has been disclaimed.

[21] Appl. No.: 259,999

[22] Filed: May 4, 1981

Related U.S. Application Data

[63] Continuation-in-part of Ser. No. 236,221, Feb. 19, 1981, abandoned.

[51] Int. Cl.$^3$ .................. C07D 233/54; C07D 405/14
[52] U.S. Cl. .................................... 548/336; 549/268; 549/60; 548/526; 548/248; 548/214; 548/374; 548/236; 548/201; 548/125; 548/127; 548/256
[58] Field of Search .................. 260/326.34; 548/336, 548/526

[56] References Cited

U.S. PATENT DOCUMENTS 4,148,883 4/1979 Celmer et al. ............... 260/239 AL
4,351,769 9/1982 Whaley et al. ...................... 548/374
4,363,922 12/1982 Magerlein et al. ................. 548/526

OTHER PUBLICATIONS

Celmer, W. C. et al., *J. Am. Chem. Soc.* 102, (1980), 4203–4209.

Magerlein et al., The Journal of Antibiotics, vol. 35, No. 2, p. 254–255, Feb. 1982.

*Primary Examiner*—Jane I. Fan
*Attorney, Agent, or Firm*—Roman Saliwanchik

[57] ABSTRACT

Novel antibacterially-active analogs of the antibiotics nodusmicin and nargenicin $A_1$. These compounds are prepared by selectively blocking active hydroxyl groups at the 9, 11 and 18 positions of nodusmicin, and the 11 and 18 positions of nargenicin $A_1$. Antibacterially-active compounds can be used in various environments to control or eradicate susceptible bacteria. The techniques for such use are well known in the art.

8 Claims, No Drawings

NARGENICIN DERIVATIVES

DESCRIPTION

Cross Reference To A Related Application

This is a continuation-in-part of my copending application Ser. No. 236,221, filed on Feb. 19, 1981 now abandoned.

BACKGROUND OF THE INVENTION

Antibiotic nodusmicin (U-59,761) is producible in a fermentation under controlled conditions using a biologically pure culture of the microbe *Saccharopolyspora hirsuta* strain 367, NRRL 12045. This antibiotic is active against various bacteria, including *Mycobacterium avium, S. lutea, K. pneumoniae, B. fragilis,* and *C. perfringens.* The structural formula for nodusmicin is shown in Chart I as compound (1).

Antibiotic nargenicin $A^1$ is disclosed in U.S. Pat. No. 4,148,883, and also described by W. D. Celmer et al., *J. Am. Chem. Soc.*, 1980, 102, 4203–4209. The structural formula for nargenicin $A^1$ is shown in Chart VI as compound (14).

BRIEF SUMMARY OF THE INVENTION

Antibacterially-active analogs of nodusmicin and nargenicin $A_1$ are obtained by techniques requiring the selective blocking of certain active hydroxyl groups, transformation of the open hydroxyl group, and removal of the blocking groups. Generally, the intermediate hydroxyl blocked compounds do not have significant antibacterial activity.

Using the above-noted general scheme, antibacterially-active analogs at the C-9, C-11, and C-18 positions of nodusmicin, and the C-11 and C-18 positions of nargenicin $A_1$, are obtained.

DETAILED DESCRIPTION OF THE INVENTION

C-18 Analogs of Nodusmicin (Chart I)

Although in many cases the order of reactivity of the hydroxyls present in nodusmicin is 18>9>11, it is frequently difficult to introduce a substituent at the 18 position in satisfactory yield or purity due to competing reactions at other hydroxyls. For this reason a compound in which the 9 and 11 hydroxyls are blocked, but the 18-hydroxyl is available, is desired. Such a compound is intermediate (4). This intermediate is prepared from nodusmicin (1) by first converting nodusmicin to 18-O-blocked nodusmicin (2). The hydroxyls at C-9 and 11 of diol (2) are then blocked with a blocking agent of such a nature that $R_1$ may be removed at C-18 while leaving the protecting group at 0-9 and 0-11 intact. The preferred blocking group for 0-9 and -11 is trichloroethoxycarbonyl ($-COOCH_2CCl_3$). Other suitable blocking groups are disclosed in Chart I. Treatment of (3)

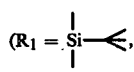

$R_2=COOH_2CCl_3$) with dilute acid (preferred) or $Bu_4NF$ in THF affords key intermediate (4).

Transformations of the 18-hydroxyl of (4) include oxidation to the ketone which may be followed by reaction with a variety of ketonic reagents; direct halogenation to 18-halo derivatives; conversion to sulfonate esters; and also replacement of the tosyl by azide whose reduction leads to amino and substituted amino compounds.

Oxidation to the ketone can be efficiently carried out under mild conditions by the use of pyridinium dichromate in aprotic medium according to the method of E. J. Corey and G. Schmidt, *Tetrahedron Lett.,* 1979, 339–402. The ketone group can be reacted with a variety of ketonic reagents as described in "Rodd's Chemistry of Carbon Compounds," 2nd Ed., S. Coffey, ed., Vol. Pt. 1, Elsevier Publishing Company, New York, 1965, pp. 52–80.

Halogenation of 18-halo derivatives can employ processes using triphenylphosphite dihalides as described by D. G. Coe, S. R. Landauer and H. N. Rydon, *J. Chem. Soc.,* 1954, 2281–2288.

An amino group can be introduced at C-18 by first conversion to the sulfonate ester as described by M. L. Wolfrom in "Carbohydrate Chemistry," Vol. 1a, 2nd ed., W. Pigman and D. Horton, Editors, Academic Press, New York, 1972, pp. 217–251. Replacement of the sulfonate by azide followed by reduction affords the amine. See L. A. Freiberg, *J. Org. Chem.,* 30, 2576 (1965), Y. Ali and A. C. Richardson, *Carbohydrate Res.,* 5, 441–448 (1967). Other references to this procedure are Houben-Weyl, "Methoden des Organismchen Chemie," Vol. XI, Part 1, Georg Thieme Verlag, Stuttgart, 1957. C. A. Buehler and D. E. Pearson, "Survey of Organic Synthesis," Wiley-Interscience, New York, N.Y., 1970. Disclosed herein are examples of the one-step conversion of the 18-hydroxyl to the azide by the process of B. Lal, B. N. Pramanik, M. S. Manhas, and A. K. Bose, *Tetrahedron Letters,* 1977–1980 (1977).

Conversion of the 18-hydroxyl group to the methyl ether can be accomplished by treating the substrate with an alkyl halide in DMF in the presence of a base such as silver oxide according to the method of R. Kuhn, H. Trischmann and I. Lou, *Angew Chem.,* 67, 32 (1955); R. Kuhn and H. Baer, *Ber.* 88, 1537 (1955); 89, 504 (1956).

Inversion of the 18- or 9-hydroxyl group can be done as described by A. K. Bose, B. Lal, W. A. Hoffman III, and M. S. Manhas, *Tetrahedron Letters,* 1973, 1619 and references cited therein. This method involves esterifying the 18- or 9-hydroxyl with inversion using diethylazodicarboxylate, triphenylphosphine and a carboxylic acid. The resulting ester can then be saponified to give the 18- or 9-hydroxy group in the opposite configuration to that in the starting compound.

Another procedure to obtain the inversion, hereinafter referred to as the epi- compound, is reduction of the oxo-compound with a reducing agent, for example, a borohydride such as sodium cyanoborohydride which is preferred.

Compounds of formula (5) which are included in this invention are shown in Chart I. Removal of the blocking groups from (5) with $Zn-NH_4Cl-MeOH$ affords (6). The 9-hydroxyl can then be acylated to afford desired analogs (7). Such compounds are shown in Chart I.

C-11 Analogs of Nodusmicin (Chart II)

The hydroxyl at C-11 is usually the least reactive of the three hydroxyls present in nodusmicin. Therefore, to introduce a substituent in good yield at that position an intermediate blocked at 0-18 and 0-9 is useful. Such an intermediate is (8). The preferred blocking group is t-butyldimethylsilyl.

Transformations may then be brought about at C-11 as described for C-18 in the above section to afford (9). Removal of the blocking groups followed by esterification results in analogs (11). Chart II shows this process.

C-9 Analogs of Nodusmicin (Chart III)

These analogs are prepared by a similar procedure to that described for the C-18 and C-11 analogs. The most reactive hydroxyl of nodusmicin at C-18 is blocked, preferably by the t-butyldimethylsilyl group to form (2). The 9-hydroxyl group is selectively reacted to afford (12). Removal of the blocking groups affords analogs (13).

thylaminopyridine [A. Hassner and V. Alexanian, *Tet. Letters*, 4475 (1978) and F. E. Ziegler and G. D. Berger, *Sym. Comm.*, 9, 539 (1979)]. The esterified products are usually isolated as a glass and characterized by cmr and high resolution ms.

Blocking groups are removed by treatment with fluoride ion ($Bu_4NF$) in tetrahydrofuran (THF) by the method of Corey [E. J. Corey and A. Venrateswarlu, *J. Amer. Chem. Soc.*, 94, 6190 (1972).] or with dilute acid to afford the appropriate ester. Purification is achieved by chromatography over silica gel.

In vitro antibacterial testing data, as measured by standard dipped disc agar diffusion assays and Minimum Inhibitory Concentration (MIC) determinations are as follows:

| | Agar Diffusion 1 mg/ml- 0.5 in. disc (mm) | | MIC (mg/ml) | | | | | | | | S. aureus SQ-Mouse $CD_{50}$ (mg/kg) |
|---|---|---|---|---|---|---|---|---|---|---|---|
| Compound | S. aureus | S. lutea | S. aureus 76 | S. aureus 6685 | S. aureus 6690 | S. faecalis 694 | S. viridans 153 | S. pyogenes 152 | S. pneumoniae 41 | K. pneumoniae 58 | |
| 21 | NZ | NZ | >100 | >100 | >100 | >100 | >100 | 100 | >100 | >100 | |
| 24 | 29 | 31 | .39 | .39 | .39 | >100 | >100 | 12.5 | >100 | >100 | 107 |
| 25 | 35 | 41 | .39 | .39 | .39 | >100 | >100 | >100 | >100 | >100 | 152 |
| 29 | 26 | 33 | | | | | | | | | |
| 32 | 29 | 32 | .78 | 1.56 | 1.56 | >100 | 25 | 25 | 12.5 | >100 | >100 |
| 35 | | 30 | | | | | | | | | |
| Nargenicin $A_1$ | | | .2 | .2 | .2 | >100 | 100 | >100 | >100 | >100 | 17-20 |

Analogs of nodusmicin within the scope of the subject invention are shown in Chart I as $R_3$ and $R_4$. $R_1$ and $R_2$ define the blocking groups and $R_5$ the esters. The subject invention encompasses analogs and esters at all three hydroxyls selectively as shown herein. As stated above, the elegant use of blocking groups is necessary to make these new and useful compounds.

C-11 and C-18 Analogs of Nargenicin $A_1$ (Chart VI and VII)

Analogs of nargenicin $A_1$ at C-11 and C-18 can be prepared by using the procedures disclosed for making similar analogs of nodusmicin (Chart VI). 18-Azido-18-deoxynargenicin$_1$ (29) and its 18-amino companion (30) can be prepared as outlined in Chart VII.

Alternatively, the above-described analogs of nargenicin $A_1$ can be prepared from nodusmicin by using procedures disclosed herein. These syntheses are shown in Chart VIII.

A blocking group, as used herein, is one which will be removed prior to the obtention of the end product. It should be understood that at times an acyl group can function as a blocking group.

Exemplified herein is the use of the t-butyldimethylsilyl ether (BDM) at C-9 and C-18. Other trisubstituted silyl ethers, for example, trimethylsilyl, triethylsilyl, methyl-di-isopropylsilyl or t-butyl-diphenylsilyl can be used. Other means to block the C-9 and C-18 hydroxyl include substituted and unsubstituted tetrahydropyranyl ethers, $\beta,\beta,\beta$-trichloroethyl ether, $\beta$-methoxyethoxymethyl ether, carbonate esters, such as t-butoxycarbonyl, benzyloxycarbonyl, substituted benzyloxycarbonyl, $\beta,\beta,\beta$-trichloroethoxycarbonyl, and the like.

Two methods of esterification can be employed. Where acid chlorides are available, the acid chloride-pyridine esterification procedure is used. Generally, the hydroxyl compound is treated with 1-3 molar equivalents of acid, 1.1-3.3 molar equivalents of dicyclohexylcarbodiimide and 0.1-0.3 moles of 4-dime- The compounds of the invention are active against *S. aureus*, and, thus, they can be used to disinfect washed and stacked food utensils contaminated with this bacterium. Further, the antibacterially-active analogs of nodusmicin and nargenicin A, can be used as bacteriostatic rinses for laundered clothes, and for impregnating papers and fabrics; and, they are also useful for suppressing the growth of sensitive organisms in plate assays and microbiological media. These uses are well-known in the antibiotic art. Accordingly, bacteriological techniques are readily available to persons skilled in this art to practice such uses.

Acids which can be used in the esterification of nodusmicin are as disclosed above, and as shown in Chart I. In its broadest aspect, carboxylic acids suitable for esterification include (a) saturated or unsaturated, straight or branched chain aliphatic carboxylic acids, for example, acetic, propionic, butyric, isobutyric, tert-butylacetic, valeric, isovaleric, caproic, caprylic, decanoic, dodecanoic, lauric, tridecanoic, myristic, pentadecanoic, palmitic, margaric, stearic, acrylic, crotonic, undecylenic, oleic, hexynoic, heptynoic, octynoic acids, and the like; (b) saturated or unsaturated, alicyclic carboxylic acids, for example, cyclobutanecarboxylic acid, cyclopentanecarboxylic acid, cyclopentenecarboxylic acid, methylcyclopentenecarboxylic acid, cyclohexanecarboxylic acid, dimethylcyclohexanecarboxylic acid, dipropylcyclohexanecarboxylic acid, and the like; (c) saturated or unsaturated, alicyclic aliphatic carboxylic acids, for example, cyclopentaneacetic acid, cyclopentanepropionic acid, cyclohexaneacetic acid, cyclohexanebutyric acid, methylcyclohexaneacetic acid, and the like; (d) aromatic carboxylic acids, for example, benzoic acid, toluic acid, naphthoic acid, ethylbenzoic acid, isobutylbenzoic acid, methylbutylbenzoic acid, and the like; and (e) aromatic-aliphatic carboxylic acids, for example, phenylacetic acid, phenylpropionic acid, phenylvaleric acid, cinnamic acid, phenylpropiolic acid and naphthylacetic acid, and the like. Suitable, halo-, nitro-, hydroxy-, amino-, cyano-, thiocyano-, and lower alkoxyhydrocarbon carboxylic acids include hydrocarboncarboxylic acids as given above which are substituted by one or more of halogen, nitro, hydroxy, amino, cyano, or thiocyano, or loweralkoxy, advantageously loweralkoxy of not more than six carbon atoms, for example, methoxy, ethoxy, propoxy, butoxy, amyloxy, hexyloxy, and isomeric forms thereof. Examples of such substituted hydrocarbon carboxylic acids are:
mono-, di-, and trichloroacetic acid;
α- and β-chloropropionic acid;
α- and γ-bromobutyric acid;
α- and δ-iodovaleric acid;
mevalonic acid;
2- and 4-chlorocyclohexanecarboxylic acid;
shikimic acid;
2-nitro-1-methyl-cyclobutanecarboxylic acid;
1,2,3,4,5,6-hexachlorocyclohexanecarboxylic acid;
3-bromo-2-methylcyclohexanecarboxylic acid;
4- and 5-bromo-2-methylcyclohexanecarboxylic acid;
5- and 6-bromo-2-methylcyclohexanecarboxylic acid;
2,3-dibromo-2-methylcyclohexanecarboxylic acid;
2,5-dibromo-2-methylcyclohexanecarboxylic acid;
4,5-dibromo-2-methylcyclohexanecarboxylic acid;
5,6-dibromo-2-methylcyclohexanecarboxylic acid;
3-bromo-3-methylcyclohexanecarboxylic acid;
6-bromo-3-methylcyclohexanecarboxylic acid;
1,6-dibromo-3-methylcyclohexanecarboxylic acid;
2-bromo-4-methylcyclohexanecarboxylic acid;
1,2-dibromo-4-methylcyclohexanecarboxylic acid;
3-bromo-2,2,3-trimethylcyclopentanecarboxylic acid;
1-bromo-3,5-dimethylcyclohexanecarboxylic acid;
homogentisic acid, o-, m-, and p-chlorobenzoic acid;
anisic acid;
salicylic acid;
p-hydroxybenzoic acid;
β-resorcylic acid;
gallic acid;
veratric acid;
trimethoxybenzoic acid;
trimethoxycinnamic acid;
4,4'-dichlorobenzilic acid;
o-, m-, and p-nitrobenzoic acid;
cyanoacetic acid;
3,4- and 3,5-dinitrobenzoic acid;
2,4,6-trinitrobenzoic acid;
thiocyanoacetic acid;
cyanopropionic acid;
lactic acid;
ethoxyformic acid (ethyl hydrogen carbonate);
and the like.

Acids which can be used to make esters considered to be the most preferred are, for example,
pyrrole-3-carboxylic,
4-bromo-2-pyrrolecarboxylic,
5-bromo-2-pyrrolecarboxylic,
4-nitropyrrole-2-carboxylic,
4-aminopyrrole-2-carboxylic,
4-methoxy-2-pyrrolecarboxylic,
4-hydroxy-2-pyrrolecarboxylic,
5-hydroxy-2-pyrrolecarboxylic,
4-methylpyrrole-2-carboxylic,
2-methylpyrrole-3-carboxylic,
thiophene-2-carboxylic,
thiophene-3-carboxylic,
3-chloro-thiophene-2-carboxylic,
5-nitro-thiophene-2-carboxylic,
amino thiophene-2-carboxylic,
3-methoxythiophene-2-carboxylic,
3-bromothiophene-2-carboxylic,
3-methylthiophene-2-carboxylic,
2-acetylaminothiophene-3-carboxylic,
3-methylthiophene-2-carboxylic,
2-methylthiophene-3-carboxylic,
4-bromomethylthiophene-3-carboxylic,
4-methoxymethylthiophene-3-carboxylic,
4-methylthioethylthiophene-3-carboxylic,
furoic,
3-furoic,
4-bromofuroic,
5-nitrofuroic,
5-aminofuroic,
4-methoxy-5-methyl-2-furoic,
4-hydroxyfuroic,
5-methylthiofuroic,
5-ethylfuroic,
and the like.

Acids which can be used to make esters considered to be preferred are, for example,
imidazole-2-carboxylic,
4-imidazolecarboxylic,
5-methyl-2-imidazolecarboxylic,
4-(or 5)-amino-5-(or 4)-imidazolecarboxylic,
histidine,
pyrazole-3-carboxylic,
pyrazole-4-carboxylic,
4-bromopyrazole-3-carboxylic,
3-methylpyrazole-5-carboxylic,
2-thiazolecarboxylic,
4-thiazolecarboxylic,
5-thiazolecarboxylic,
iso-oxazole-3-carboxylic,
isooxazole-5-carboxylic,
oxazole-4-carboxylic,
1,2,3-triazole-4-carboxylic,
and the like.

The above acids are well-known and available to those skilled in the art.

PREPARATION OF ANTIBIOTIC NODUSMICIN

Part A. Fermentation

A biologically pure culture of *Saccharopolyspora hirsuta* strain 367, NRRL 12045, is used to inoculate 500-ml. Erlenmeyer seed flasks containing 100 ml. of sterile medium consisting of the following ingredients:

| | |
|---|---|
| Glucose monohydrate | 25 g./l. |
| Pharmamedia* | 25 g./l. |
| Tap water q.s. | 1 liter |

*Pharmamedia is an industrial grade of cottonseed flour produced by Traders Oil Mill Company, Fort Worth, Texas.

The seed medium presterilization pH is 7.2. The seed inoculum is grown for three days at 28° C. on a Gump rotary shaker operating at 250 rpm and having a 2½ inch stroke.

After three days incubation, the seed medium is used to inoculate (the inoculation rate is 5 ml. of seed inoculum per 100 ml. of fermentation medium) a series of 500-ml. Erlenmeyer flasks containing sterile fermentation medium consisting of the following ingredients:

| | |
|---|---|
| Glucose monohydrate | 10 g./l. |
| Dextrin | 20 g./l. |
| Corn steep liquor | 2.5 g./l. |
| NH4NO3 | 3.0 g./l. |
| NaCl | 2.0 g./l. |
| CaCO3 | 5.0 g./l. |
| pH-7.2 (presterilization) | |

The fermentation flasks are incubated at a temperature of 28° C. on a Gump rotary shaker operating at 250 rpm and having a 2½ inch stroke. Harvest is usually after about 5 days of fermentation. A typical 5 day fermentation has the following titers of antibiotic in the fermentation broth:

| Day | S. lutea Assay, Bu/ml. |
|---|---|
| 2 | 8.0 |
| 3 | 10.4 |
| 4 | 10.4 |
| 5 | 11.2 |

In the assay results, a biounit (BU) is defined as the concentration of the antibiotic which gives a 20 mm. zone of inhibition under the standard assay condition. Thus, if, for example, a fermentation beer has to be diluted 1/100 to give a 20 mm. zone of inhibition, the potency of such beer is 100 Bu/ml.

B. Recovery and Purification

The whole beer (ca. 5,000 l.) from a fermentation, as described above, is adjusted to pH 7.3 with NaOH and filtered on a 30 inch filter press using diatomaceous earth as a filter aid. During the filtration operation wash water is applied to the filter cake. From the filtration operation is recovered 5,500 l. of clear fermentation broth which is then extracted twice with methylene dichloride (1,400 l. each time) to give a total of 2.800 l. of solvent extract. This solvent extract is concentrated in vacuo to 10 l. Assay on a standard S. lutea disc plate assay gives a value of 2,424 Bu/ml.

The extract concentrate described above (9 l.), is chromatographed over a column containing 9 kg. of silica gel (E. Merck-silica gel 7734). The column is eluted as follows:

20 liters methylene dichloride; then 40 liters 2% methanol in methylene dichloride; then 150 liters 5% methanol in methylene dichloride, then 100 liters 10% methanol in methylene dichloride. Four liter fractions are collected after an 80 liter forerun. Fractions 10–19 contain antibiotic nodusmicin. Crystalline antibiotic nodusmicin (41.4 g.) is obtained on concentration of fractions 10–19. Another 12.8 g. of crystalline antibiotic nodusmicin is obtained by chromatography of the mother liquors over silica gel with ethyl acetate as eluant.

PREPARATION OF ANTIBIOTIC NARGENICIN A1

Nargenicin A1 can be prepared by the procedures disclosed in U.S. Pat. No. 4,148,883.

The following examples are illustrative of the products and process of the invention, but are not to be construed as limiting. All percentages are by weight and all solvent mixture proportions are by volume unless otherwise noted.

EXAMPLE 1

18-O-(t-Butyldimethylsilyl)nodusmicin (2a) and 9,18-O-Di-(t-butyldimethylsilyl)nodusmicin (9a)

A solution of 2.16 g (5.12 mmol) of nodusmicin, 1.7 g (25 mmol) of imidazole, and 1.5 g (10 mmol) t-butyldimethylsilyl chloride in 25 ml of DMF is kept at ambient temperature for 18 hrs. The solvent is distilled under vacuum. The residue is dissolved in methylene dichloride and washed several times with water. The solution is dried and concentrated. Chromatography over 105 g of silica gel using chloroform-ethyl acetate (2:1) for elution affords 645 mg (19.4%) of diether (9a) and 1.787 g (65.1) of 18-O-ether (2a).

Observed exact mass of molecular ion for (9a) was 650.4034 (calculated for $C_{35}H_{62}O_7Si_2$, 650.4034); for (2a) the observed was 536.3160 (calculated for $C_{29}H_{48}O_7Si$, 536.3169).

CMR data are referenced to the OCH3 (23) group at 1136.8 Hz unless otherwise noted.

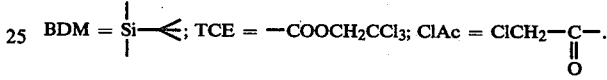

BDM = ; TCE = —COOCH2CCl3; ClAc = ClCH2—C—.

EXAMPLE 2

18-O-(t-Butyldimethylsilyl)-9,11,-O-di($\beta,\beta,\beta$-trichloroethoxycarbonyl) nodusmicin (3a)

$\beta,\beta,\beta$-Trichloroethyl chloroformate (497 mg, 2.4 mmole) is added dropwise with stirring to a cooled solution of 574 mg (1.07 mmole) of silyl ether (2a) in 2 ml of pyridine. A gummy precipitate forms which is dispersed by the addition of 5 ml of acetone. An additional 150 mg (0.71 mmole) of reagent is added. After 30 min. the reaction mixture is diluted with methylene dichloride and washed successively with dilute acid, water, and sodium hydroxide and dried. The residue remaining on evaporation of the solvent is chromatographed over 35 g of silica gel using Skellysolve B (isomeric hexanes)-ethyl acetate (10:1) for elution. A fraction of 700 mg (73.8%) which shows one spot on TLC is obtained.

CMR (acetone —d6) δ-3.83, —2.73; 11.81, 15.27, 16.43, 17.75, 20.69, 25.54, 32.14, 32.75, 34.41, 38.60, 42.74, 45.89, 56.84, 67.67, 76.51, 76.54, 78.22, 78.35, 80.45, 81.43, 82.41, 89.47, 94.99, 126.65, 132.01, 133.39, 153.43, 153.60, 172.49.

EXAMPLE 3

9,11-O-Di($\beta,\beta,\beta$-trichloroethoxycarbonyl) nodusmicin (4a)

A solution of 634 mg (0.72 mmole) of silyl ether (3a) in 20 ml of tetrahydrofuran (THF) containing 3 ml of N HCl is refluxed for 3 hr. The THF is evaporated and the residue extracted with methylene dichloride. After concentration of the dried solution, a residue of 595 mg of crude product remains. Chromatography over 35 g of silica gel using Skellysolve-B:ethyl acetate (2:1) for elution affords 423 mg (76.3%) of di-ester (4a).

Exact mass of M+: Calcd for $C_{29}H_{36}Cl_6O_{11}$: 770.0389. Observed: 770.0353.

CMR (acetone d6) δ11.71, 15.21, 16.33, 20.84, 32.05, 32.88, 34.28, 38.60, 42.36, 45.86, 56.83, 65.19, 76.47, 77.85, 78.14, 80.31, 81.36, 82.40, 89.37, 94.88, 126.51, 132.37, 133.06, 133.28, 153.36, 153.62, 172.48.

EXAMPLE 4

9,11-O-Di($\beta,\beta,\beta$-trichloroethoxycarbonyl)-18-O-thiobenzoylnodusmicin (5a)

Three ml of oxalyl chloride is added to a solution of 1.49 g (10 mmole) of dimethylbenzamide in 20 ml of methylene dichloride. After stirring for 1.5 hr the solvent is evaporated under vacuum. The residue is dissolved in methylene dichloride and evaporated. This process is repeated twice. The crystalline residue is dissolved in sufficient solvent to give a solution of 1 mmole/2 ml.

Two ml of the above reagent is added to 600 ml (0.78 mmole) of alcohol (4a) and 93 mg (1.18 mmole) of pyridine in 15 ml of methylene dichloride. After 1 hr, 1 ml of pyridine is added. Hydrogen sulfide is passed into the solution for 5 min. The reaction mixture is diluted with methylene chloride and washed with dilute acid, bicarbonate and dried. The residue obtained on evaporation of the solvent is chromatographed over 35 g of silica gel using Skellysolve-B:ethyl-acetate (3-1) for elution. A fraction of 340 mg is obtained whose CMR spectrum was compatible with structure (5a).

CMR (acetone —$d_6$) $\delta$11.74, 14.77, 15.38, 16.29, 32.08, 33.08, 34.24, 38.30, 42.53, 45.93, 56.84, 57.83, 76.50, 89.36, 94.91, 126.138, 153.37, 153.59, 172.43, 209.

EXAMPLE 5

18-O-Thiobenzoylnodusmicin (6c)

A mixture of 300 mg (0.34 mmole) of thioester (5a), 300 mg NH$_4$Cl and 600 mg of Zn in 10 ml of methanol is stirred in an ice bath for 0.5 hr. The solids are removed by filtration and the methanol distilled under vacuum. Chromatography of the residue over 30 g of silica gel while eluting with chloroform:methanol (30:1) affords 59 mg (32%) of thioester (6c).

Exact mass of M+: Calcd for $C_{30}H_{38}O_7S$: 542.2338. Observed 542.2323.

CMR (acetone d-6) $\delta$12.08, 14.76, 15.44, 16.76, 33.07, 34.95, 35.64, 38.30, 43.22, 49.87, 56.84, 72.03, 74.96, 75.98, 76.83, 83.27, 84.94, 88.75, 128.4, 128.45, 132.25, 133.28, 136.69, 172.25, 209.

EXAMPLE 6

18-Deoxynodusmicin (6a)

Tributyltin hydride (0.2 ml) is added to a refluxing solution of 59 mg (0.11 mmole) of thioester (6c) in 5 ml of THF. In about 10 min the yellow color disappears. The solvent is evaporated and the residue chromatographed over 6 g of silica gel. The column is eluted with Skellysolve-B:ethyl acetate (1:1) to afford 15 mg of 18-deoxynodusmicin (6a). Exact mass of M+: Calcd for $C_{23}H_{34}O_6$; 406.2355. Found: 406.2344.

EXAMPLE 7

18-O-(t-Butyldimethylsilyl)-9,11,O-di(tetrahydropyranyl)nodusmicin (3c)

To a solution of 350 mg (0.65 mmole) of silyl ether (2a) in 1 ml of dihydropyran and 5 methylene dichloride is added 5 mg of toluene sulfonic acid (TSA). After 0.75 hr the reaction mixture is washed with potassium bicarbonate, dried and concentrated. Chromatography over 35 g of silica gel (Skellysolve B:ethyl acetate (10:1) leads to the isolation of 114 mg of ether (3c).

EXAMPLE 8

9,11-O-Di(tetrahydropyranyl)nodusmicin (4c)

Ether (3c) (114 mg) is dissolved in 2 ml of THF and 2 ml of 1 M Bu$_4$NF in THF added. After 1 hr the solvent is evaporated. The residue is partitioned between water and ether. Evaporation of the other affords THP ether (4c).

EXAMPLE 9

18-Chloro-18-deoxy-9,11-O-di($\beta,\beta,\beta$-trichloroethoxycarbonyl)nodusmicin (5b)

A solution of 492 mg (0.64 mmole) of dicarbonate (4a) and 359 mg of triphenylphosphine in 15 ml of acetonitrile and 5 ml of carbon tetrachloride is stirred at ambient temperature for 45 min. The solvent is evaporated and the residue dissolved in methylene dichloride. After washing with potassium bicarbonate, the solution is dried and concentrated. The residue, when chromatographed over 35 g of silica gel (Skellysolve B:ethyl acetate, 3:1), gives 372 mg (73.5%) of chloride (5b).

Anal. calcd for $C_{29}H_{35}Cl_7O_{10}$: Cl, 31.35. Found: 30.78. Exact mass of M+: Calcd for $C_{29}H_{35}{}^{35}Cl_7O_{10}$: 788.0050. Observed: 788.0026.

CMR (acetone d-6; Referenced to TMS) $\delta$12.35, 15.36, 16.97, 22.29, 32.76, 33.85, 34.93, 39.29, 42.93, 46.57, 55.45, 57.59, 72.25, 78.16, 78.78, 81.03, 81.97, 83.13, 90.00, 95.56, 127.21, 132.14, 133.89, 134.59, 154.03, 154.28, 172.93.

This chlorination can be done by other methods known in the art [see Reagents for Organic Synthesis by L. F. Fieser and M. Fieser], for example, by the use of thionyl chloride, phosphorus trichloride, phosphorus pentachloride, triphenylphosphine dichloride or triphenylphosphite dichloride.

EXAMPLE 10

18-Chloro-18-deoxynodusmicin (6b) (U-62,270)

A mixture of 366 mg (0.46 mmole) of chloride (5b), 350 mg NH$_4$Cl, and 700 mg Zn in 15 ml of methanol is stirred at ambient temperature for 10 min. The reaction mixture is filtered. The filtrate is diluted with methylene dichloride, washed with water, dried and concentrated. Chromatography over 30 g of silica gel (Skellysolve B: ethyl acetate-1:1) gives 135 mg (66.7%) of chloride (6b).

Anal. calcd. for $C_{23}H_{33}ClO_6$: Cl, 8.04, Found: 7.63. Exact mass of M+: Calcd for $C_{23}H_{33}{}^{35}ClO_6$, 440.1965. Found: 446.1957.

CMR (acetone d-6) $\delta$12.54, 14.46, 16.62, 21.58, 33.06, 34.82, 35.32, 38.17, 42.65, 49.58, 54.83, 56.84, 71.88, 74.78, 78.30, 82.71 84.69, 88.68, 128.31, 129.84, 132.36, 135.95, 172.66.

A 0.5 inch disc dipped into a methanol solution of chloride (6b) at a concentration of 1 mg/ml gave a zone of inhibition of 30 mm when spotted on an agar tray seeded with *S. lutea.*

EXAMPLE II

18-O-(t-Butyldimethylsilyl)-9,11-O-di(chloroacetyl)nodusmicin (3b)

Chloroacetic anhydride (512 mg. 3 mmoles) is added to a solution of 536 mg (1 mmole) of ether (2a) in 5 ml of methylene dichloride and 1 ml of pyridine. After 1 hr at ambient temperature, water and methylene dichloride are added. The organic layer is washed with acid, water, and bicarbonate. The solution is dried and concentrated. Chromatography over 35 g of silica gel (Skellysolve B:ethyl acetate 2:1) yields 552 mg (80.3%) of diester (3b).

Exact mass of M+: Calcd for $C_{33}H_{50}O_9{}^{35}Cl_2Si$, 688.2601. Found: 688.2526.

CMR (acetone d-6) δ −3.95, −2.86, 11.91, 15.37, 16.45, 20.71, 17.79, 25.60, 32.09, 32.78, 34.48, 38.99, 40.83, 41.02, 42.91, 46.29, 56.83, 67.87, 75.03, 78.08, 78.62, 80.64, 82.85, 89.51, 126.94, 132.06, 133.44, 166.57, 172.49.

EXAMPLE 12

9,11-O-Di(chloroacetyl)nodusmicin (4b)

A solution of 50 mg of ether (3b) in 5 ml of THF and 1 ml N HCl is refluxed. After 2 hr TLC on silica gel using Skellysolve B:ethyl acetate (2:1) for elution shows no ether (3b) but a slower spot assigned structure (4b).

EXAMPLE 13

9,18-O-Di(t-butyldimethylsilyl)-11-chloro-11-deoxynodusmicin (10a)

A solution of 650 mg (1 mmole) of diether (9a) in 2 ml of pyridine and 15 ml of acetonitrile is treated with 0.1 ml of thionyl chloride. After 15 min at room temperature the mixture is refluxed for 30 min. The solvent is evaporated and the residue dissolved in methylene dichloride. This solution is washed with dilute acid, water, bicarbonate and dried. The residue from evaporation of the solvent is chromatographed over 35 g of silica gel (Skellysolve B:ethyl acetate (11:2). A fraction of 249 mg is obtained which contains the desired material. This fraction is rechromatographed over 35 g of silica gel using chloroform-methanol (0.5%) for elution. A fraction of 40 mg of chloride (10a) is obtained.

Anal. calcd for $C_{35}H_{61}ClSi_2O_6$: Cl, 5.29. Found: Cl, 5.39. Exact mass of M+: Calcd for $C_{35}H_{61}O_6{}^{35}ClSi_2$, 668.3695. Found: M+ 668.3674.

CMR (acetone d-6) δ −3.89, −2.42, 14.33, 15.21, 15.1, 15.31, 17.73, 20.67, 25.35, 32.59, 32.88, 33.03, 34.25, 42.45, 51.36, 56.83, 64.55, 67.52, C-72.82, 78.27, 82.56, 84.72, 88.64, 128.02, 132.78, 132.60, 172.

This chlorination can be carried out by a variety of other methods known in the art. For example, triphenylphosphine and $CCl_4$, triphenylphosphite dichloride, phosphorus trichloride, or phosphorus pentachloride may be used.

EXAMPLE 14

9,18-O-Di-(t-butyldimethylsilyl)-11-deoxy-11-oxonodusmicin (10b)

To a suspension of 564 mg (1.5 mmole) of pyridinium dichromate in 10 ml of methylene dichloride is added 640 mg (1 mmole) of diether (9a) and 0.5 g of pulverized A-4 molecular sieves. After 30 min, ether is added. The mixture is filtered through a pad of silica gel and evaporated to give 508 mg (79.6%) of ketone 10b.

The oxidation can be done by the use of other reagents known in the art [see Fieser and Fieser, op. cit.], for example by other chromic mediated oxidation or by dimethylsulfoxide mediated oxidation.

EXAMPLE 15

9,11-O-Di(β,β,β-trichloroethoxycarbonyl)-18-O-p-toluenesulfonylnodusmicin (5C)

p-Toluenesulfonyl chloride (1.4 mmole) is added at ambient temperature to a stirred solution of 1 mmole of 9,11-O-di-(β,β,β-trichloroethoxycarbonyl)nodusmicin (4a) in 5 ml of pyridine. After 17 hrs methylene dichloride is added and the mixture washed successively with dilute acid, water, and sodium bicarbonate. After drying and evaporation of the solvent, the residue is purified by chromatography over 35 g of silica gel using chloroform-methanol (30:1) for elution. Fractions are combined on the basis of TLC profile to afford sulfonate (5C).

EXAMPLE 16

9,11-O-Di(β,β,β-trichloroethoxycarbonyl)-18-O-methanesulfonylnodusmicin (5d)

In the manner described in Example 15, 1 mmole of (4a) is treated with 1.4 mmole of methanesulfonyl chloride to afford (5d) following work up and chromatography.

EXAMPLE 17

9,11-O-Di(β,β,β-trichloroethoxycarbonyl)-18-epi-chloro-18-deoxynodusmicin (5e)

Triphenylphosphite dichloride is prepared by the procedure of D. G. Coe, S. R. Landover, and H. N. Rydon, J. Chem. Soc. (1954) 2281. When 1 mmole of dicarbonate (4a) is treated in 5 ml of methylene dichloride solution with 1.1 mmole of this reagent in the manner described in the aforementioned reference, there is obtained, after chromatography over 35 g of silica gel, the 18-epi-chloro analog (5e).

EXAMPLE 18

9,11-O-Di(β,β,β-trichloroethoxycarbonyl)-18-deoxy-18-oxonodusmicin (5f)

To a suspension of 1.5 mmole of pyridinium dichromate in 10 ml of methylene dichloride is added 1 mmole of (4a) and 0.5 g of pulverized A-4 molecular sieves. After 0.5 hr, ether is added and the mixture filtered through a pad of filter aid. The filtrate is evaporated to give essentially pure ketone (5f). Greater purity can be achieved by chromatography over silica gel using chloroform:methanol (30:1) for elution.

The oxidation can be done by the use of other reagents known in the art [see Fieser and Fieser, op. cit.], for example by other chromic mediated oxidation or by dimethylsulfoxide mediated oxidation.

EXAMPLE 19

9,11-O-Di(β,β,β-trichloroethoxycarbonyl)-18-epi-nodusmicin (5g)

One mmole of 18-ketone (5f) prepared as described in Example 18, is added with stirring to a cooled mixture of 200 mg of sodium borohydride in 5 ml of 2-propanol. After 30 min, dilute mineral acid is added. The solvent is evaporated in vacuo. The residue is dissolved in methylene dichloride, washed with water, dried and concentrated. Chromatography over 35 g of silica gel using chloroform 1% methanol for elution affords the epi-alcohol.

This reduction can be done by other mild methods known in the art (Fieser and Fieser, op. cit.), for example using sodium cyanoborohydride.

EXAMPLE 20

9,11-O-Di(β,β,β-trichloroethoxycarbonyl)-18-chloro-18-deoxynodusmicin (5H)

Chlorination of epi-alcohol 5 g with triphenylphosphite dichloride in the manner described for the synthesis of (5f) affords the title compound (5H).

EXAMPLE 21

9,11-O-Di(β,β,β-trichloroethoxycarbonyl)-18-azido-18-deoxy-nodusmicin (5i)

A solution of 1 mmole of 18-tosylate (5c) and 500 mg of sodium azide in 10 ml of DMF is heated at 90° for 10 hrs with stirring. The solvent is removed under vacuum. The residue is partitioned between water-methylene dichloride. The organic fraction after concentration is chromatographed over 35 g silica gel to afford azide (5i) when eluted with chloroform-methanol (1%).

EXAMPLE 22

9,11-O-Di(β,β,β-trichloroethoxycarbonyl)-18-amino-18-deoxynodusmicin (5j)

To a solution of 1 mmole of azide (5i) in 5 ml of 2-propanol is added 250 mg of sodium borohydride. After 30 min at ambient temperature the excess hydride is destroyed by addition of dilute acid. The solvent is evaporated. Purification of the residue by chromatography over 35 g of silica gel affords amine (5j).

The azide can be reduced with other reagents known in the art, for example by metal catalysts with hydrogen, by hydrogen sulfide, by triphenyl phosphine.

EXAMPLE 23

9,11-O-Di(β,β,β-trichloroethoxycarbonyl)-18-deoxy-18-methylenenodusmicin (5k)

Treatment of 1 mmole of 18-ketone (5f) with 2 mmole of triphenylphosphine methylene prepared in ether from methyltriphenylphosphonium bromide and butyl lithium leads, after chromatography of the crude product, to 18-methylene compound (5k).

Other methylene transfer agents known in the art can also be used, for example sulfoniummethides.

EXAMPLE 24

Removal of $R_2$ Blocking Groups from Compounds (5c)–(5k) to Give Comparable Compounds of Structure (6)

The blocked compounds 5c-5k (1 mmole) are dissolved in 10 ml of methanol and while stirring in an ice bath 300 mg of $NH_4Cl$ and 600 mg of Zn dust is added. The mixture is filtered after 30 min. The filtrate is evaporated in vacuo. The residue is dissolved in methylene chloride and chromatographed over 35 g of silica gel using chloroform-methanol (1–3%) for elution.

EXAMPLE 25

Acid-Carbodiimide Procedure for Esterification of Compound (6) to Compound (7)—(Chart I)

Upon reacting compound (6) with 1–3 molar equivalents of thiophene-3-carboxylic acid, 1.1–3.3 molar equivalents of dicyclohexycarbodiimide and 0.1–0.3 moles of 4-dimethylaminopyridine, there is obtained compound (7).

EXAMPLE 26

Acid Chloride-Pyridine Procedure for Esterification of Compound (6) to Compound (7)

Upon reacting a cooled solution of compound (6) in pyridine with an excess of acid chloride there is obtained compound (7).

EXAMPLE 27

18-O-(t-Butyldimethylsilyl)nargenicin $A_1$ (15)

A solution of 505 mg (1.0 mmole) of nargenicin $A_1$, 314 mg (2.1 mmoles) of t-butyldimethylsilyl chloride and 306 mg (5.2 mmoles) of imidazole in 6 ml of DMF is maintained at ambient temperature for 3 days. The reaction mixture is poured in $H_2O$ and extracted several times with ether. After washing the ether with water and drying, it is concentrated in vacuo. The residue is chromatographed over 35 g of silica gel using Skellysolve B-ethyl acetate (2:1) for elution. The yield of silyl ether (15) is 478 mg (76.0%). Exact mass of $M^+$: Calcd for $C_{34}H_{51}NO_8Si$: 629.3383. Found: $M^+$ 629.3333.

CMR (acetone d-6) δ −3.5, −2.7, 12.64, 15.42, 16.84, 17.74, 20.81, 25.57, 32.61, 34.46, 34.85, 39.27, 43.02, 49.63, 56.84, 67.62, 73.39, 75.09, 78.77, 81.44, 82.66, 89.32, 109.82, 115.41, 122.37, 123.66, 127.70, 130.83, 132.98, 135.01, 159.94, 172.67.

EXAMPLE 28

18-O-(t-Butyldimethylsilyl)-11-O-(β,β,β-trichloroethoxycarbonyl)nargenicin $A_1$ (16)

β,β,β-Trichloroethylchloroformate (0.316 ml, 1.5 mmole) is added to a solution of 626 mg (1 mmole) of silyl ether (15) in 5 ml methylene dichloride and 2 ml of pyridine. After 25 min., ice is added and the reaction mixture worked up in the usual manner to give a quantitative yield of (16) which shows one spot on tlc moving slightly faster than ether (15). This material is used in the next step without further purification.

EXAMPLE 29

11-O-(β,β,β-Trichloroethoxycarbonyl)nargenicin $A_1$ (17)

The crude ether (16) from Example 28 (770 mg. 0.96 mmole) is dissolved in 30 ml of THF and 3 ml of N HCl. The solution is refluxed for 2.5 hr. The solvent is evaporated and the residue partitioned between $MeCl_2$ and $H_2O$. The organic layer is separated, washed with $KHCO_3$, dried and concentrated. Chromatography over 35 g of silica gel using Skellysolve B-ethyl acetate (2:1) for elution affords 494 mg of carbonate (17). The yield on the two-step process is 71.6%.

Exact mass of $M^+$; Calcd for $C_{31}H_{38}{}^{35}Cl_3NO_{10}$: 689.1561. Found $M^+$ 689.1534.

CMR (acetone d-6) δ 12.04, 15.22, 16.39, 20.83, 32.15, 32.90, 34.40, 38.70, 42.48, 46.04, 56.83, 65.27, 72.56, 76.42, 77.96, 81.13, 82.04, 82.50, 89.17, 94.93, 110.01, 115.95, 121.92, 123.83, 126.90, 132.18, 133.12, 133.30, 153.75, 159.51, 172.57.

EXAMPLE 30

18-Chloro-18-deoxy-11-O-(β,β,β-trichloroethoxycarbonyl)nargenicin $A_1$ (22)

A solution of 493 mg (0.71 mmole) of carbonate (17), 400 mg (1.43 mmoles) of triphenylphosphine in 15 ml of acetonitrile and 15 ml of carbon tetrachloride is stirred at ambient temperature for 30 min. The solvent is evaporated and the residue partitioned between methylene dichloride and water. The methylene dichloride solution is washed with potassium bicarbonate, dried and concentrated. Chromatography over 40 g of silica gel yields 387 mg (76.7%) of chloride (22).

Exact mass of M+: Calcd for $C_{31}H_{37}{}^{35}Cl_4NO_9$, 707.1222. Found: M+ 707.1246.

CMR (acetone d-6; referenced to TMS) 12.72, 15.41, 17.08, 22.35, 32.92, 33.96, 35.08, 39.44, 43.09, 46.83, 55.60, 57.60, 73.20, 77.19, 78.31, 81.95, 82.71, 83.33, 89.89, 110.62, 116.61, 123, 124.45, 127.71, 132.07, 133.79, 134.92, 154, 160, 173.07.

EXAMPLE 31

18-Deoxy-18-oxo-11-O-($\beta,\beta,\beta$-trichloroethoxycarbonyl)nargenicin $A_1$ (23)

Pyridinium dichromate (1.26 mmoles, 474 mg) is added to a stirred solution of 580 mg (0.84 mmole) of carbonate (17) in 10 ml of methylene dichloride containing 500 mg of ground A-b 4 molecular sieves. After 2.5 hrs the reaction mixture is diluted with ether and filtered. The filtrate is refiltered through a small pad of silica gel to give a colorless solution. Evaporation of the solvent affords 511 mg (88.4%) of ketone (23) which shows one spot on TLC (Skellysolve B-ethyl acetate, 2:1).

Exact mass of M+; Calcd for $C_{31}H_{36}{}^{35}Cl_3NO_{10}$, 687.1405. Found: M+ 687.1443.

CMR (acetone d-6; referenced to TMS) δ 12.64, 16.36, 16.94, 28.35, 32.72, 34.04, 34.89, 39.23, 43.08, 46.74, 57.47, 75.07, 77.06, 79.96, 81.82, 82.59, 83.26, 89.76, 95.53, 110.56, 116.56, 122.56, 124.47, 127.67, 130.59, 133.73, 136.04, 154.35, 160.07, 172.45.

EXAMPLE 32

18-Deoxy-18-oxonargenicin $A_1$ (25)

A mixture of 1.0 g (1.45 mmole) of ketone (23), 100 mg of ammonium chloride and 200 mg of zinc dust is stirred in 5 ml of methanol for 25 min. The mixture is filtered and concentrated. The residue is shaken with methylene dichloride and water. The organic layer is separated, dried and concentrated. Chromatography over 40 g of silica gel (chloroform-ethyl acetate, 2:1) affords 705 mg (94.8% of ketone (25).

Exact mass of M+: $C_{28}H_{35}NO_8$, 513.2362. Found: M+ 513.2354.

CMR (acetone d-6; referenced to TMS) δ 13.20, 16.45, 17.47, 28.34, 34.12, 35.10, 35.38, 39.81, 43.51, 50.34, 57.50, 73.97, 75.63, 80.49, 82.14, 83.49, 89.96, 110.46, 116.08, 123.01, 124.35, 128.41, 129.34, 133.54, 137.65, 160.58, 172.64, 186.75.

EXAMPLE 33

18-Chloro-18-deoxynargenicin $A_1$ (24)

A mixture of 326 mg (0.46 mmole) of chloride (22), 350 mg of ammonium chloride and 700 mg of zinc dust in 10 ml of methanol is stirred for 10 min. The zinc is removed by filtration and the filtrate worked up as described previously. The crude product is chromatographed over 35 g of silica gel (Skellysolve B-ethyl acetate, 4:1) to give 160 mg (65.1%) of ketone (24).

Exact mass of M+; Calcd for $C_{28}H_{36}{}^{35}ClN_7$, 533.2180. Found: 533.2188.

EXAMPLE 34

18-O-(t-Butyldimethylsilyl)-11-chloro-11-deoxynargenicin $A_1$ (18)

Triphenylphosphite dichloride (1.2 mmoles, 456 mg) is added to a solution of 629 mg (1 mmole) of silyl ether (15) in 15ml of methylene dichloride. After 15 min the reaction mixture is washed with potassium bicarbonate. Chromatography over 40 g of silica gel (Skellysolve B-ethyl acetate, 4:1) gives partial purification, but the product has a strong phenolic odor. Therefore, it is rechromatographed over 35 g of silica gel using chloroform methanol (40:1) for elution. An improved product of 537 mg (83.0%) (Compound 18) is obtained which shows one spot on tlc using several systems, but still shows extra aromatic bands in the CMR.

CMR (acetone d-6, referenced to TMS) δ $-3.22$, $-2.68$, 14.23, 15.89, 18.21, 21.31, 26.07, 32.75, 33.15, 34.20, 34.63, 42.92, 51.81, 57.42, 64.65, 67.98, 67.98, 78.67, 81.79, 83.05, 89.31, 110.28, 116.16, 122.76, 124.38, 128.03, 132.86, 133.38, 134.56, 160.44, 173.04.

EXAMPLE 35

18-O-(t-Butyldimethylsilyl)-11-deoxy-11-oxonargenicin $A_1$ (19)

Pyridinium dichromate (564 mg, 1.5 mmole) is added to a stirred solution of 629 mg (1 mmole) of ether (15) in 10 ml of methylene dichloride containing 0.5 g of powdered 4-A molecular sieves. After one hour, the mixture is diluted with ether and filtered through a pad of filter aid. The filtrate is passed through a column of 35 g of silica gel and eluted with Skellysolve B-ethyl acetate (4:1). A fraction of 461 mg (73.5%) of ketone (19) is obtained.

Exact mass of M+: Calcd for $C_{34}H_{49}NO_8Si$: 627.3227. Found: 627.3216.

CMR (acetone d-6 referenced to TMS) δ 8.91, 15.66, 15.92, 18.35, 21.45, 26.17, 33.14, 34.10, 40.36, 41.85, 43.26, 57.62, 60.60, 67.97, 74.48, 79.03, 82.48, 83.00, 88.89, 110.54, 116.58; 122.42, 124.50, 126.81, 134.00, 134.32, 134.82, 159.91, 173.10, 184.31.

EXAMPLE 36

11-Deoxy-11-oxonargenicin $A_1$ (21)

A solution of 282 mg of ketone (19) in 13 ml of dioxane and 3 ml of N $H_2SO_4$ is refluxed for 15 min. The dioxane is evaporated and the product extracted with methylene dichloride. Chromatography over 30 g of silica gel leads to the obtention of 221 mg (96.4%) of ketone (21), mp 221-223.

Exact mass of M+: Calcd for $C_{28}H_{35}NO_8$: 513.2362. Found: 513.2349.

CMR (acetone d-6; referenced to TMS) δ 8.92, 15, 71, 21.70, 33.43, 34.13, 40.48, 41.85, 43.38, 57.67, 60.67, 65.86, 74.69, 79.01, 82.53, 83.09, 89.00, 110.73, 116.76, 123, 124.79, 126.89, 133.91, 134.41, 135.12, 160, 173.25, 184.07.

EXAMPLE 37

11-Chloro-11-deoxynargenicin $A_1$ (20)

Tetrabutylammonium fluoride (approx. 2.5 mmole) is added to a solution of 610 mg (0.94 mmole) of chloride (18) in 15 ml of THF. After 45 min, the THF is distilled in vacuo. The residue is partitioned between ether and water. The ether solution is dried and evaporated. The residue is chromatographed over 35 g of silica gel (Skellysolve B-ethyl acetate-2:1) to give 213 mg (42.5%) of chloride (20).

Exact mass of M+: Calcd. for $C_{28}H_{36}{}^{35}ClNO_7$: 533.2180. Found: 533.2188.

CMR (acetone d-6, referenced to TMS) δ 14.35, 15.85, 16.03, 21.54, 33.17, 33.71, 34.60, 34.96, 43.23, 52.22, 57.72, 65.09, 65.95, 73.33, 78.94, 82.20, 83.37, 89.73, 110.54, 116.55, 124, 124.79, 128.41, 133.17, 133.71, 135.11, 161, 173.57.

EXAMPLE 38

18-O-(t-Butyldimethylsilyl)-11-O-(tetrahydropyranyl)-nargenicin A₁ (26)

Dihydropyran (2 ml) and 256 mg of TSA are added to a solution of 4.32 g (6.85 mmoles) of silyl ether (15) in 40 ml of methylene dichloride. The solution is stirred for 0.5 hr. The reaction mixture is washed with $KHCO_3$, dried, and concentrated; two chromatograms over 240 g of silica gel, respectively (Skellysolve B-ethyl acetate, 4:1) yields 1.518 g (31.0%) of isomer A and 1.483 g (30.36%) isomer B of (26).

Exact mass of M+: Calcd for $C_{39}H_{59}NO_9Si$, 713.3959. Found: Isomer A, 713.3935; Isomer B, 715.3949.

EXAMPLE 39

11-O-(Tetrahydropyranyl)nargenicin A₁ (27)

An excess of tetrabutylammonium fluoride is added to a solution of 266 mg (0.37 mmole) of isomer A of ether (26) in 9 ml of THF. After 30 min the reaction mixture is worked up as described in Example 37 to give after chromatography over 20 g of silica gel (Skellysolve B-ethyl acetate, 2:1), 213 mg (96.1%) of ether (27).

In a similar manner, 160 mg of isomer B gave 61 mg of isomeric ether (27).

Exact mass of M+: Calcd for $C_{33}H_{45}NO_9$, 599.3094. Found: Isomer A, 599.3068; Isomer B, 599.3080.

EXAMPLE 40

18-Azido-18-deoxy-11-O(tetrahydropyranyl)nargenicin A₁ (28)

To a solution of 993 mg (1.65 mmoles) of ether (27) [Isomer A] in 100 ml of THF is added 890 mg (3.39 mmoles) of triphenylphosphine and 600 mg (3.44 mmoles) of diethylazodicarboxylate. This is followed by the addition of 940 mg (3.42 mmoles) of diphenylphosphoryl azide in 30 ml of THF. After 1.5 hrs the solvent is evaporated and the residue chromatograhed over 40 g of silica gel (Skellysolve B-ethyl acetate, 2:1) to give 949 mg (83.4%) of (28) (Isomer A).

CMR (acetone d-6; referenced to TMS) δ 12.96, 15.16, 16.23, 17.25, 21.77, 25.99, 31.65, 33.76, 34.54, 35.23, 40.23, 44.36, 50.08, 57.11, 57.34, 64.91, 73.94, 79.36. 81.86, 84.06, 84.27, 90.17, 104,23, 110.39, 116.11, 123.03, 124.15, 128.32, 130.00, 134.02, 136.64, 160.37 172.53.

Treatment of 1.191 g (1.98 mmoles) of Isomer B in the manner described above affords 0.855 g (69.2%) of azide, Isomer B. It gives a comparable CMR.

EXAMPLE 41

18-Azido-18-deoxynargenicin A₁ (29)

A solution of 920 mg (1.47 mmoles) of azide (28) in 20 ml of methanol in 2.25 ml of N $H_2SO_4$ is stirred at ambient temperature overnight. The solvent is evaporated and the residue dissolved in methylene dichloride-water. The methylene chloride solution is separated, dried and concentrated. The residue is chromatographed over 40 g of silica gel (Skellysolve B-ethyl acetate, 3:1) to afford 510 mg (64.2%) of azide (29).

CMR (acetone d-6 referenced to TMS) δ 13.15, 14.75, 15.05, 17.14, 33.71, 35.03, 35.19, 39.84, 44.46, 50.40, 57.34, 61.72, 74.10, 75.68, 79.64, 82.07, 84.25, 89.91, 110.48, 116.09, 123.00, 124.41, 128,46, 129.80, 133.94, 136.44, 160.66, 172.66.

Similar hydrolysis of isomer B gives the identical azide.

EXAMPLE 42

18-O-Thiocarbonyl-1′-imidazolenargenicin A₁ (31)

A mixture of 7.21 g of nargenicin A₁ (14), and 2.85 g of 1,1′-thiocarbonyl diimidazole in 350 ml of THF is refluxed for 4 hr. The reaction is monitored by TLC and when a significant amount of product is present the reaction is stopped. The solvent is removed under vacuum. The residue is chromatographed (chloroform-ethyl acetate, 2:1) over 240 g of silica gel to afford 5.5 g (63.1%) of 18-O-thioimidazolenargenicin A₁ (31).

CMR δ (acetone-$d_6$) 13.24, 16.04, 16.13, 17.41, 33.56, 35.13, 35.40, 39.91, 43.94, 50.46, 57.51, 74.08, 75.65, 76.25, 80.17, 82.20, 83.96, 90.04, 110.51, 116.19, 119.02, 123.09, 124.48, 129.54, 137.68, 128.57, 131.57, 133.78, 137.19, 160.69, 172.77, 184.31. Exact mass: M+ calcd for $C_{32}H_{39}N_3O_8S$: 625.2458. Found: 625.2429.

EXAMPLE 43

18-Deoxynargenicin A₁ (32)

Thioimidazole (31) (5.5 g, 9.0 mmole), in 76 ml of THF is added in portions to a refluxing solution of 15.2 ml of $Bu_3SnH$ in 152 ml of THF. The mixture is refluxed for 20 min after the last addition. The THF is removed under vacuum and the residue is triturated two times with 25 ml portions of Skellysolve B. The white solid thus obtained is chromatographed over 240 g of silica gel using chloroform-methanol (1%) to give 1.51 g (33.5%) of 18-deoxynargenicin A₁ (32).

CMR δ (acetone-$d_6$) 10.54, 12.56, 14.85, 16.61, 23.00, 33.89, 34.34, 34.56, 39.17, 43.63, 49.70, 56.55, 73.44, 75.04, 78.28, 81,36, 83.63, 89.28, 109.84, 115.42. 122.31, 123.72, 127.70, 129.59, 133.30, 135.10, 160.00, 172.40. Exact mass: M+calcd for $C_{28}H_{37}NO_7$; 499.2546. Found: 499.2570.

EXAMPLE 44

18-Chloro-18-deoxy-9,11-O-di(β,β,β-trichloroethoxycarbonyl)nodusmicin (33)

Dicarbonate (4b) (492 mg, 0.64 mmole) and 359 mg (1.37 mmole) of triphenylphosphine in 15 ml of acetonitrile and 5 ml of carbon tetrachloride is stirred at ambient temperature for 45 min. The solvent is evaporated and methylene dichloride and potassium bicarbonate solution added. The crude product is chromatographed over 35 g of silica gel (Skellysolve B-ethyl acetate, 3:1). The yield of chloride (33) is 372 mg (73.5%).

Anal calcd for $C_{29}H_{35}Cl_7O_{10}$: Cl 31.35. Found: Cl 30.78. Exact mass of M+: Calcd for $C_{29}H_{35}{}^{35}Cl_7O_{10}$: 788.0050. Found 788.0026.

CMR (acetone d-6, referenced to TMS) δ 12.35, 15.36, 16.97, 22.29, 32.76. 33.85, 34.93, 39.29, 42.93, 46.57, 55.45, 57.59, 77.25, 78.16, 78.78, 81.03, 81.97, 83.13, 90.00, 95.56, 127.21, 132.14, 133.89, 134.59, 154.08, 154.23, 172.93.

EXAMPLE 45

18-Chloro-18-deoxynodusmicin (35)

A mixture of 366 mg of chloride (33), 350 mg of ammonium chloride, and 700 mg zinc dust in 10 ml of methanol is stirred at room temperature for 10 min. The reaction mixture is filtered and concentrated. Following the usual work up (see Example 10) and chromatography over 30 g of silica gel (Skellysolve B-ethyl acetate, 1:1) there is obtained 135 mg (66.7%) of chloride (35).

Anal calcd for $C_{23}H_{33}ClO_6$: Cl, 8.04. Found: Cl, 7.63. Exact mass of M+, calcd for $C_{23}H_{33}{}^{35}ClO_6$: 440.1965. Found: 440.1957.

CMR (acetone d-6) δ 12.54, 14.46, 16.62, 21.58, 33.06, 34.82, 35.32, 38.17, 42.65, 49.58, 54.83, 56.84, 71.88, 74.78, 78.30, 82.71, 84.69, 88.68, 128.31, 129.84, 132.36, 135.95, 172.66.

EXAMPLE 46

18-Chloro-18-deoxynargenicin A₁ (24)

A mixture of 440 mg (1 mmole) of chloride (35), 167 mg (1.5 mmole) a pyrrole-2-carboxylic acid, 309 mg (1.5 mmole) of dicyclohexylcarbodiimide and 12 mg of 4-dimethylaminopyridine in 15 ml of THF is stirred for 20 hrs. The reaction mixture is filtered and concentrated. Purification of the residue by chromatography over 35 g of silica gel, using Skellysolve B-ethyl acetate (2:1) for elution, leads to the isolation of the desired product (24).

EXAMPLE 47

18-Deoxy-18-oxo-9,11-O-di(β,β,β-trichloroethoxycarbonyl)nodusmicin (34)

To a solution of 384 mg (0.5 mmole) of dicarbonate (4b) in 10 ml of methylene dichloride is added 282 mg (0.75 mmole) of pyridinium dichromate. After 2 hrs the reaction mixture is diluted with ether and filtered through a pad of filter aid. The filtrate is further purified by chromatography over 25 g of silica gel using Skellysolve B-ethyl acetate, 2:1 for elution. Ketone (34) is recovered using standard procedures.

EXAMPLE 48

18-Deoxy-18-oxonodusmicin (36)

A mixture of 1 mmole of ketone (34), 400 mg of ammonium chloride, 800 mg of zinc dust in 10 ml of methanol is stirred at room temperature for 15 min. The reaction mixture is evaporated and worked up as described in Example 10. The crude product is purified by chromatography over 40 g of silica gel using Skellysolve ethyl acetate (1:1) for elution. Ketone (36) is recovered by concentration of the selected fractions.

EXAMPLE 49

18-Deoxy-18-oxonargenicin A₁ (25)

A mixture of 1 mmole of diol (36), 2 mmole of dicyclohexylcarbodiimide, 2 mmole of pyrrole-2-carboxylic acid and 0.2 mmole of 4-dimethylaminopyridine in 20 ml of THF is stirred at ambient temperature for 20 hrs. Following work-up and chromatography, as described above, the desired product (25) is recovered.

EXAMPLE 50

18-Azido-18-deoxy-9,11-O-di(tetrahydropyranyl)-nodusmicin (37)

One mmole of ether (4c), 2 mmole of triphenylphosphine, and 2.1 mmole of diethylazodicarboxylate in 15 ml of THF is treated with 2.1 mmole of diphenylphosphoryl azide. After 3 hrs at ambient temperature the reaction mixture is concentrated. Following chromatography over 30 g of silica gel (Skellysolve B-ethyl acetate (2:1), the azide (37) is identified by the usual physical data.

EXAMPLE 51

18-Azido-18-deoxynodusmicin (38)

A solution of 1 mmole of diether (37) in 6 ml of dioxane and 1 ml of 2 N $H_2SO_4$ is stirred at ambient temperature for several hours. The solution is evaporated and the residue worked up as described in Example 41. Chromatography over 30 g of silica gel using Skellysolve B-ethyl acetate for elution leads to the isolation of azide (38).

EXAMPLE 52

18-Azido-18-deoxynargenicin A₁ (29)

Esterification of 1 mmole of azide (38) with 2 mmole of pyrrole-2-carboxylic acid, 2 mmole of dicyclohexylcarbodiimide and 0.2 mmole of 4-dimethylaminopyridine in 15 ml of THF is acomplished as described in Example 46. Azide (29) is isolated by following the procedures of Example 46.

EXAMPLE 53

11-Chloro-11-deoxynodusmicin (39)

One mmole of diether (10a) is dissolved in 25 ml of dioxane and 2.5 ml of 2 N $H_2SO_4$ added. The solution is heated at 60° for several hours and then evaporated. Chloride (26) is isolated by following the procedures of Example 41.

EXAMPLE 54

11-Chloro-11-deoxy-18-O-(t-butyldimethylsilyl)nodusmidin (41)

A solution of 1 mmole of chloride (39), 5 mmole of imidazole and 2 mmole of t-butyldimethylsilyl chloride in 10 ml of DMF is maintained at ambient temperature for 18 hrs. The reaction mixture is poured into 25 ml of ice-water and extracted with ether. The ether extracts are washed several times with water, dried and concentrated. The crude product is purified by chromatography over silica gel using Skellysolve B-ethyl acetate 20:1 for elution. Chloride (41) is recovered by concentration of the selected fractions.

EXAMPLE 55

11-Chloro-11-deoxy-18-O-(t-butyldimethylsilyl)nargenicin A₁ (43)

Esterification of 1 mmole of chloride (41) using 2 mmole of pyrrole-2-carboxylic acid, 2 mmole of dicyclohexycarbodiimide and 0.2 mmole of 4-dimethylaminopyridine is accomplished as described in Example 46. Purification of the crude product by chromatography leads to the isolation of chloride (43).

EXAMPLE 56

18-Chloro-18-deoxynargenicin A₁ (20)

To a solution of 1 mmole of ether (43) in 10 ml of THF is added 2.5 mmole of tetrabutylammonium fluoride in THF. After 2 hrs at ambient temperature, the solvent is evaporated. The residue is partitioned between ether and water. The ether extract is dried and concentrated. Following chromatography over 25 g of silica gel, chloride (20) is isolated.

EXAMPLE 57

By following the procedures of Examples 53, 54, 55 and 56, but substituting the ketone (10b) in Example 53 for the chloride (10a), there are obtained the corresponding oxo compounds (40), (42), (44), and (21) as shown in Chart VIII.

EXAMPLE 58

18-Epinargenicin A₁ (45)

Tetrahydrofuran saturated with HCl was added dropwise to a solution of 460 mg (0.9 mmol) of 18-deoxy-18-oxonargenicin A₁ (25), 600 mg (9.6 mmol) of NaBH₃CN and 10 mg of methyl orange in 15 ml of THF until a pink color persisted for 10 min. The solvent was evaporated under vacuum. The residue was chromatographed over 40 g of silica gel using CHCl₃-MeOH (2%) for elution. The least polar fraction eluted weighed 153 mg (33.0% yield) and was identified as 18-epinargenicin A₁ (45). A more polar fraction of 121 mg (26.1% yield) was proven to be nargenicin A₁ (14).

Exact mass of M⁺ for epimer 45: Calcd for $C_{28}H_{37}NO_8$: 515.2519. Found: M⁺ 515.2513. ¹³C NMR (AcCH₃-d₆) δ (referenced to Me₄Si) 13.2, 15.2, 17.1, 20.7, 33.9, 34.9, 35.3, 39.8, 44.7, 50.4, 57.2, 66.8, 74.1, 75.7, 81.1, 82.0, 128.5, 130.8, 134.0, 135.5, 160.6, 172.8.

When tested on a standard agar diffusion (12.5 cm disc) test at a concentration of 1 mg/ml compound (45) gave the following zones of inhibition in mm:

| Sarcina lutea | Staphylococcus aureus |
|---|---|
| 35 | 26 |

EXAMPLE 59

18-Deoxy-18-oximinonargenicin A₁, Isomer A (46) and Isomer B (47)

A solution of 610 mg (1.18 mmol) of ketone (25) and 90 mg (1.3 mmol) of hydroxylamine hydrochloride in 11 ml of pyridine is maintained at ambient temperature for 1 hour. The solvent is evaporated in vacuo. The residue is dissolved in CHCl₃-MeOH (1:1) and again evaporated. Chromatography over 35 g of silica gel (Skellysolve B-ethyl acetate, 1:1) leads to the isolation of 107 mg (17.2%) of oxime (46) and 186 mg (30.0%) of oxime (47). In addition, 254 mg of a mixture of (46) and (47) is obtained.

Exact mass of M⁺ for Isomer A (46): Calcd for $C_{28}H_{36}N_2O_8$: 528.2471. Found: M⁺ 528.2450. ¹³C NMR (AcCH₃-d₆) δ 13.2, 16.5, 17.5, 17.7, 33.9, 35.2, 35.3, 39.9, 43.8, 50.5, 57.5, 72.1, 74.1, 75.8, 82.2, 84.1, 90.0, 110.5, 116.1, 123.1, 124.4, 128.5, 130.1, 133.8, 137.0, 155.6, 160.7, 172.3.

Exact mass of M⁺ for Isomer B (47): Found: 528.2460. ¹³C NMR (AcCH₃-d₆) δ 12.0, 13.2, 15.9, 17.0, 34.8, 35.1(2), 39.9, 45.0, 50.5, 57.3, 74.1, 75.7, 78.9, 82.1, 85.1, 90.0, 110.5, 116.1, 123.1, 124.4, 128.6, 128.9, 134.2, 137.3, 155.1, 160.7, 171.5.

EXAMPLE 60

18-Deoxy-18-semicarbazononargenicin A₁ (48)

18-Deoxyl-18-oxonargenicin A₁ (25) (300 mg. 0.58 mmol) and 72 mg (0.65 mmol) of semicarbazide hydrochloride in 5 ml of pyridine and 15 drops of H₂O is kept at room temperature for 0.5 hours. The solvent is evaporated under vacuum. The residue is dissolved in ethyl acetate, toluene is added, and the solution evaporated. The residue is chromatographed over CHCl₃-MeOH (10:1) to afford 318 mg (98.3%) of semicarbazone (48).

¹³C NMR (AcCH₃-d₆) δ 13.2, 14.2, 16.1, 17.2, 35.0(3), 39.9, 44.9, 50.5, 57.4, 74.2, 75.6, 80.6, 82.2, 84.9, 90.1, 110.5, 116.2, 123.0, 124.6, 128.6, 128.8, 134,1, 137.4, 147.3, 159.2, 160.9, 171.6.

EXAMPLE 61

18-Deoxy-18-methoximinonargenicin A₁, Isomer A (49) and Isomer B (50)

Methoxyamine hydrochloride (60 mg, 0.72 mmol) is added to a solution of 300 mg (0.58 mmol) of ketone (25) in 10 ml of pyridine. Since the reaction is incompleted in 0.5 hours, an additional 30 mg (0.36 mmol) of methoxyamine hydrochloride is added. After 0.25 hours, the solvent is evaporated under vacuum. The residue is dissolved in CHCl₃-MeOH (10:1) and again evaporated. Chromatography over 49 g of silica gel afforded 79 mg (25.1%) of isomer A (49) and 211 mg (67.1%) of Isomer B (50).

Exact mass of M⁺ for Isomer A: Calcd for $C_{29}H_{38}N_2O_8$: 542.2628. Found: 542.2615. ¹³C NMR (AcCH₃-d₆) δ 13.2, 16.4, 17.5, 17.6, 33.9, 35.1, 35.3, 39.9, 43.7, 50.4, 57.5, 61.9, 72.1, 74.1, 75.7, 82,2, 84.0, 90.0, 110.5, 116.1, 123.1, 124.4, 128.5, 129.8., 133.8, 137.3, 156.3, 160.6, 172.2.

Exact mass of Isomer B: Found: 542.2610. ¹³C NMR (AcCH₃-d₆) δ 12.5, 13.2, 15.9, 17.0, 34.7, 35.1(2), 39.9, 45.0, 57.3, 61.9, 74.1, 75.7, 78.4, 82.2, 85.0, 90.0, 110.5, 116.1, 124.2, 124.4, 128.9(2), 134.1, 137.6, 155.41, 160.6, 171.4.

The antibacterial activity of compounds (46), (47), (48), (49) and (50) on a standard agar diffusion (12.5 cm disc) test at a concentration of 1 mg/ml is shown in the following table:

| Compound | S. lutea | S. aureus |
|---|---|---|
| (46) | 37* | 30 |
| (47) | 37 | 30 |
| (49) | 35 | 30 |
| (50) | 35 | 30 |
| (48) | 35 | 28 |

*Zone size in mm.

C-18 Analogs of Nodusmicin
Chart I

-continued
C-18 Analogs of Nodusmicin
Chart I

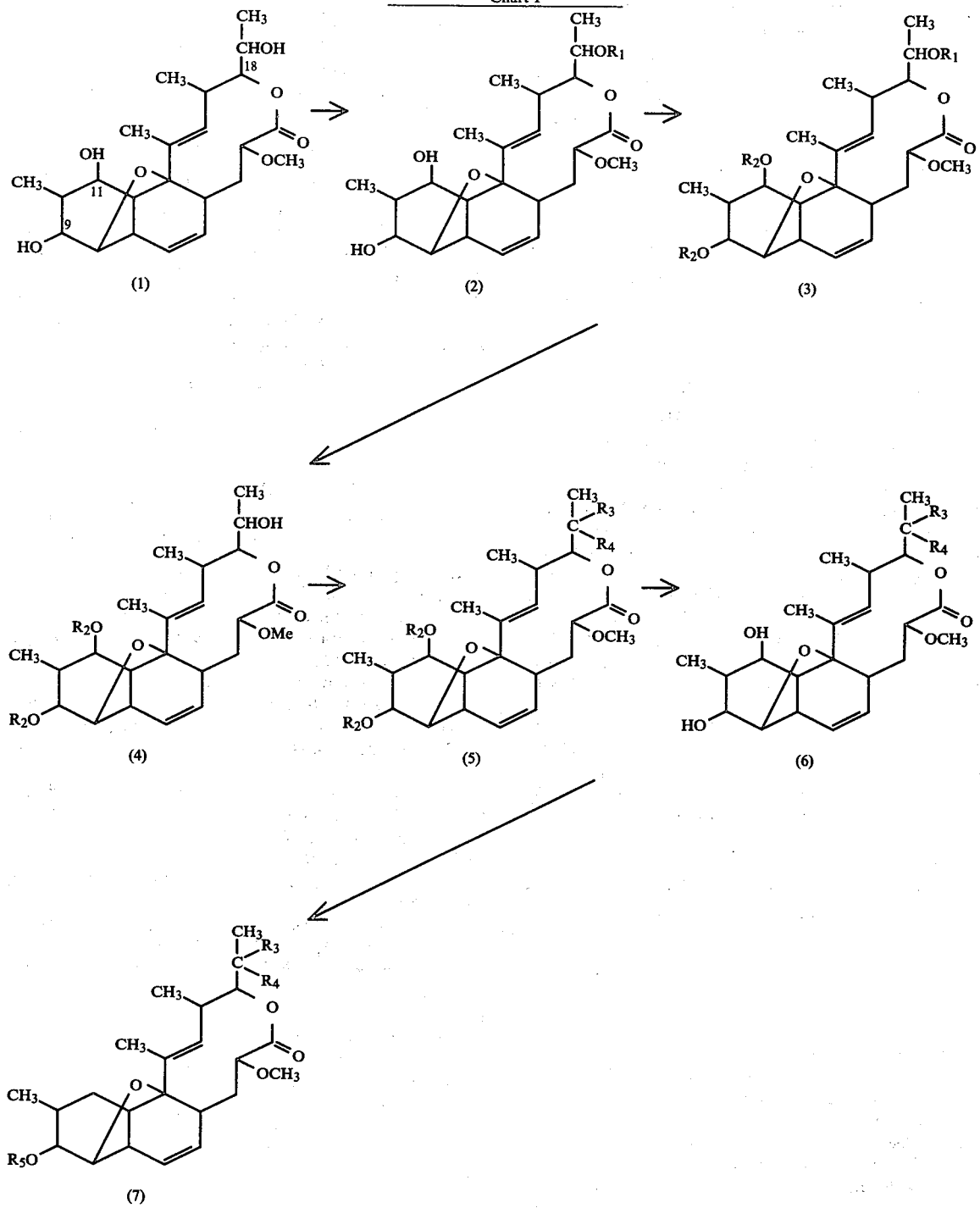

$R_1$ = blocking group selected from the group consisting of silyl ether, acyl of from 2-18 carbons, inclusive, substituted acyl wherein the acyl is as above, and the substitution group can be halo, alkyl (1-4C), phenyl, and lower-alkoxycarbonyl (1-4C).

$R_2$ = blocking group different from $R_1$ and of such a nature that it will remain intact when $R_1$ is removed; thus, it can be a compound selected from the group consisting of lower alkoxycarbonyl (1-4C), for example, —COOCH$_2$CCl$_3$ (preferred), acyl and substituted acyl, as defined above, for example, —COCH$_2$Cl (preferred), and tetrahydropyranyl ether.

$R_3$ and $R_4$ = at least one is H and the other is selected from the group consisting of H, O-arylsulfonyl, wherein aryl can be phenyl or substituted phenyl, for example, C$_6$H$_5$, p-CH$_3$—C$_6$H$_4$, p-NO$_2$C$_6$H$_4$; O-alkylsulfonyl and substituted O-alkylsulfonyl wherein alkyl is C$_1$-C$_8$ inclusive, for example, OSO$_2$CH$_3$, OSO$_2$CF$_3$; halogen, for example, Cl, Br, I, F; azide; amine and substituted amine, for example

wherein $R_6$ and $R_7$ can be H, alkyl ($C_1-C_8$, inclusive), for example, $CH_3$, $C_2H_5$,

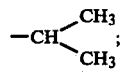

and substituted alkyl, for example, $CH_2CH_2$ halogen, $CH_2CH_2OH$, $CH_2OH$, acyl, for example, $CO(CH_2)_nCH_3$, n=0–8; S alkyl wherein alkyl is $C_1-C_8$, inclusive, for example $SCH_3$, $SCH_2CH_3$; S substituted alkyl, for example, $SCH_2CH_2OH$; nitrile (CN); thioester, for example,

wherein aryl is $C_6H_5$ and substituted $C_6H_5$ with alkyl of $C_1-C_8$, inclusive;

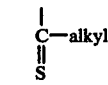

wherein alkyl is $C_1-C_8$, inclusive;

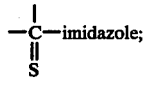

OH; O-alkyl wherein alkyl is $C_1-C_8$, inclusive;

$R_3$ and $R_4$ taken together are selected from the group consisting of =O(ketone); =$NOR_8$, wherein $R_8$ can be H, alkyl ($C_1-C_8$, inclusive), alkylidene and substituted alkylidene, for example, $CHR_9$, wherein $R_9$ is $(CH_2)_nCH_3$ and n is an integer of from 0–8, inclusive; =CH—$COOC_2H_5$; =$CHOCH_3$;

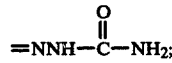

$R_3$ is OH and $R_4$ is

$R_3$ is OH and $R_4$ is alkyl of from 1 to 8 carbon atoms, inclusive;

$R_5$=

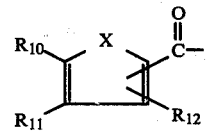

wherein X is selected from the group consisting of N, S, and O; $R_{10}$, $R_{11}$, and $R_{12}$ can be the same or different, and are selected from the group consisting of H, OH, halogen, $NO_2$, alkyl of 1–8 C, inclusive, $NH_2$, $NR_{13}R_{14}$, wherein $R_{13}$ and $R_{14}$ can be selected from the group consisting of H, OH, and alkyl and substituted alkyl, wherein the alkyl is from 1 to 8 carbon atoms, inclusive, and the substitutent on substituted alkyl can be OH, halogen, SH, and the like; O alkyl, S alkyl, O acyl, and N acyl;

Preferred:

Structures B

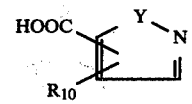

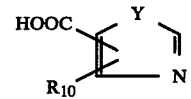

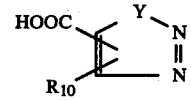

wherein Y is selected from the group consisting of NH, sulfur or oxygen; COOH can be at any one of the unoccupied ring carbon atoms; and $R_{10}$ is as defined above and can be on any one of the unoccupied ring carbon atoms, with the following exceptions:

(1) $R_3$, $R_4$ are not HOH when $R_5$ is H or pyrrole-2-carbonyl; and
(2) $R_3$ and $R_4$ are not H when $R_5$ is pyrrole-2-carbonyl.

C-11 Analogs of Nodusmicin
Chart II

-continued
C-11 Analogs of Nodusmicin
Chart II
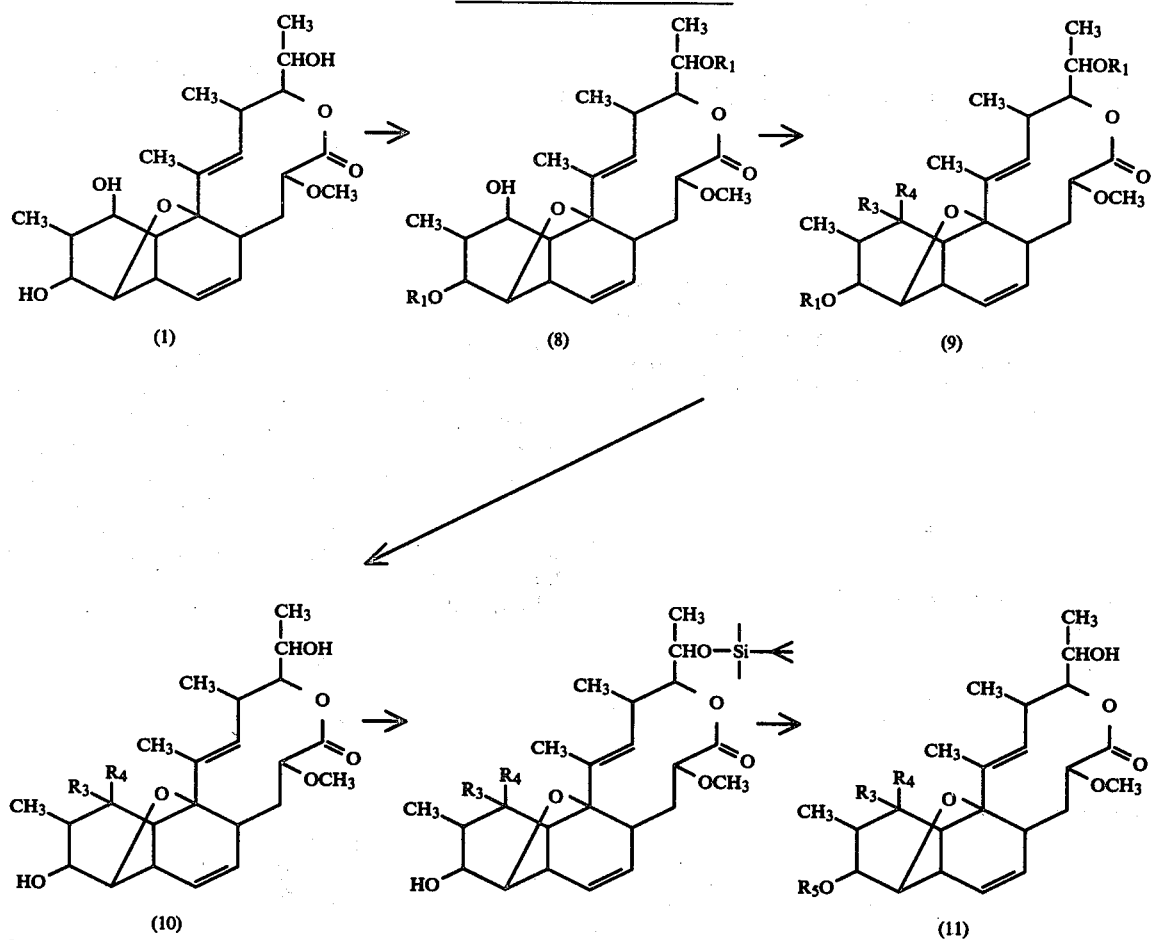
$R_1, R_2, R_3, R_4$ and $R_5$ are defined in Chart I.
C-9 Analogs of Nodusmicin
Chart III
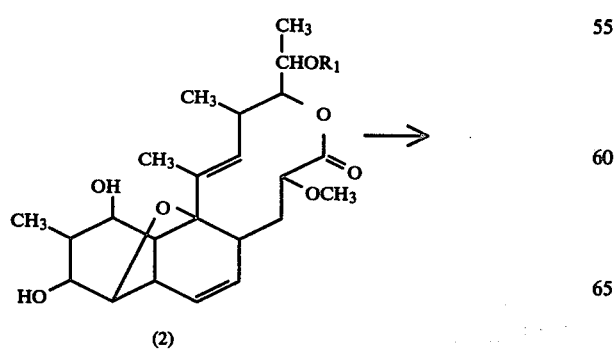
-continued
C-9 Analogs of Nodusmicin
Chart III
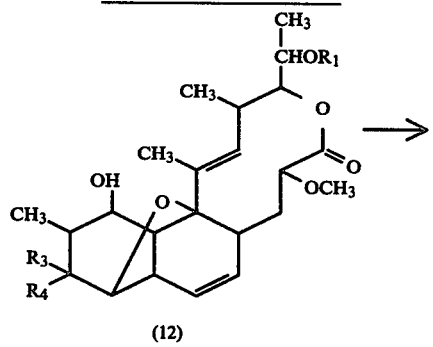

-continued
C-9 Analogs of Nodusmicin
Chart III

Chart IV

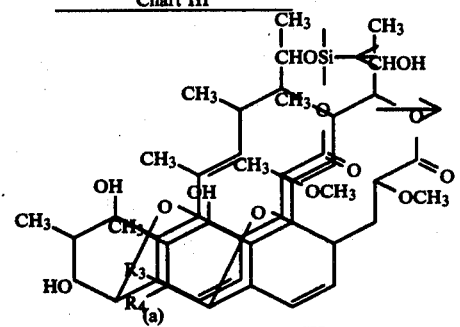

(13)

$R_1$, $R_3$, $R_4$ are defined in Chart I.

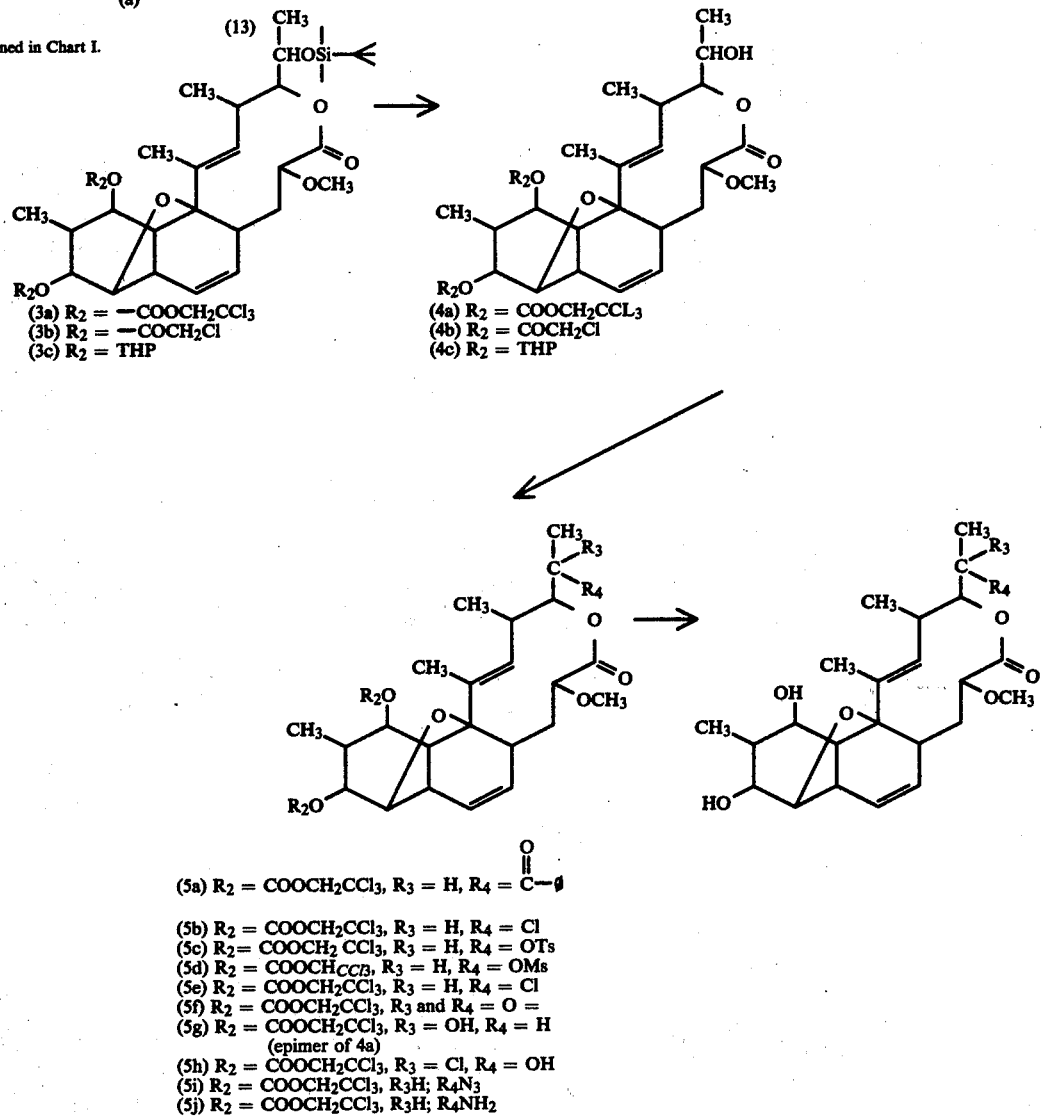

(3a) $R_2 = -COOCH_2CCl_3$
(3b) $R_2 = -COCH_2Cl$
(3c) $R_2 = THP$ (4a) $R_2 = COOCH_2CCL_3$
(4b) $R_2 = COCH_2Cl$
(4c) $R_2 = THP$ (5a) $R_2 = COOCH_2CCl_3$, $R_3 = H$, $R_4 = \overset{O}{\overset{\|}{C}}-\phi$ (5b) $R_2 = COOCH_2CCl_3$, $R_3 = H$, $R_4 = Cl$
(5c) $R_2 = COOCH_2 CCl_3$, $R_3 = H$, $R_4 = OTs$
(5d) $R_2 = COOCH_{CCl3}$, $R_3 = H$, $R_4 = OMs$
(5e) $R_2 = COOCH_2CCl_3$, $R_3 = H$, $R_4 = Cl$
(5f) $R_2 = COOCH_2CCl_3$, $R_3$ and $R_4 = O=$
(5g) $R_2 = COOCH_2CCl_3$, $R_3 = OH$, $R_4 = H$
   (epimer of 4a)
(5h) $R_2 = COOCH_2CCl_3$, $R_3 = Cl$, $R_4 = OH$
(5i) $R_2 = COOCH_2CCl_3$, $R_3H$; $R_4N_3$
(5j) $R_2 = COOCH_2CCl_3$, $R_3H$; $R_4NH_2$ -continued
Chart IV
(5k) $R_2 = COOCH_2CCl_3$, $R_3$ and $R_4 = CH_2$
(6a) $R_3 = R_4 = H$
(6b) $R_3 = H$, $R_4 = Cl$
(6c) $R_3 = H$, $R_4 = \overset{\overset{S}{\|}}{C}-C_6H_5$
Chart V
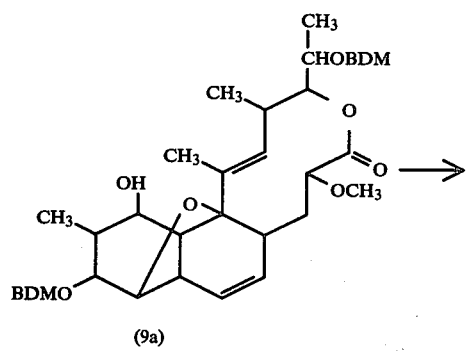
(9a)
-continued
Chart V
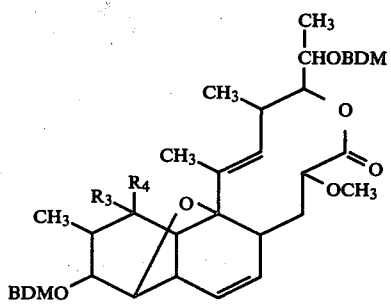
(10a) $R_3 = H$, $R_4 = Cl$
(10b) $R_3$ and $R_4 = O$
Chart VI
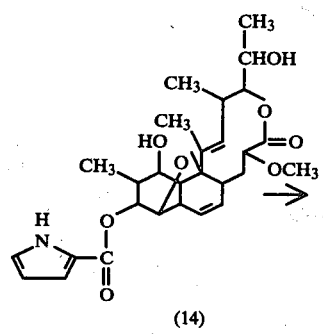
(14)
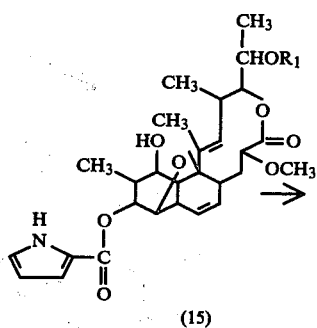
(15)
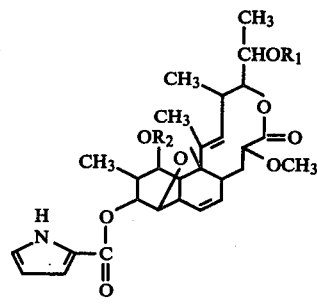
(16)
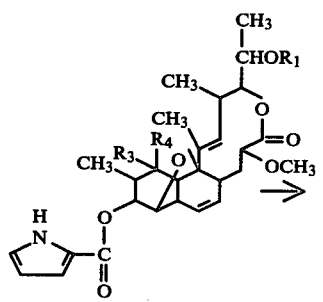
(18) $R_3 = H$
     $R_4 = Cl$
(19) $R_3$ and $R_4$ is $= O$
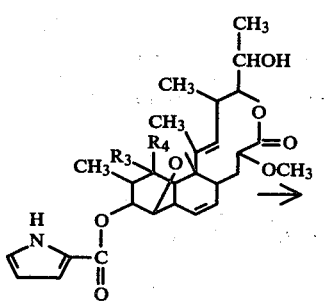
(20) $R_3 = H$
     $R_4 = Cl$
(21) $R_3$ and $R_4$ is $= O$
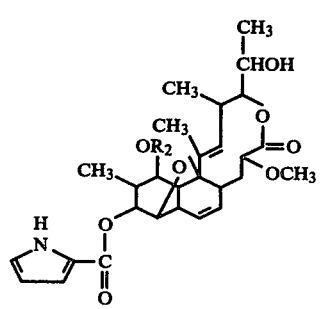
(17)

Chart VI
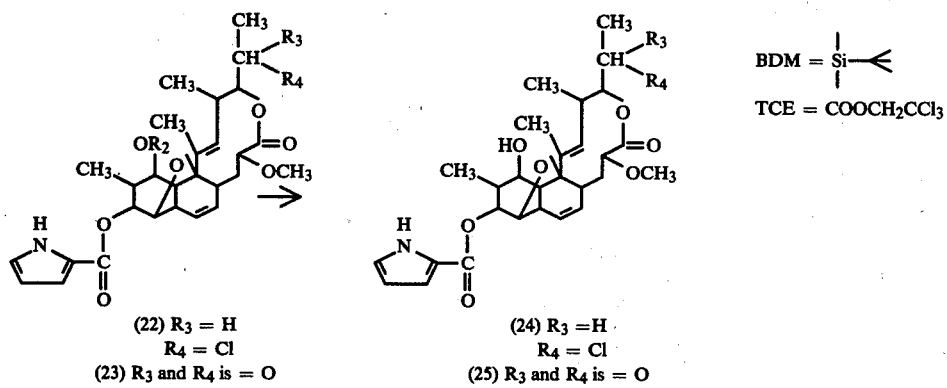
(22) R₃ = H, R₄ = Cl
(23) R₃ and R₄ is = O
(24) R₃ = H, R₄ = Cl
(25) R₃ and R₄ is = O
BDM = Si⟨
TCE = COOCH₂CCl₃
Chart VII
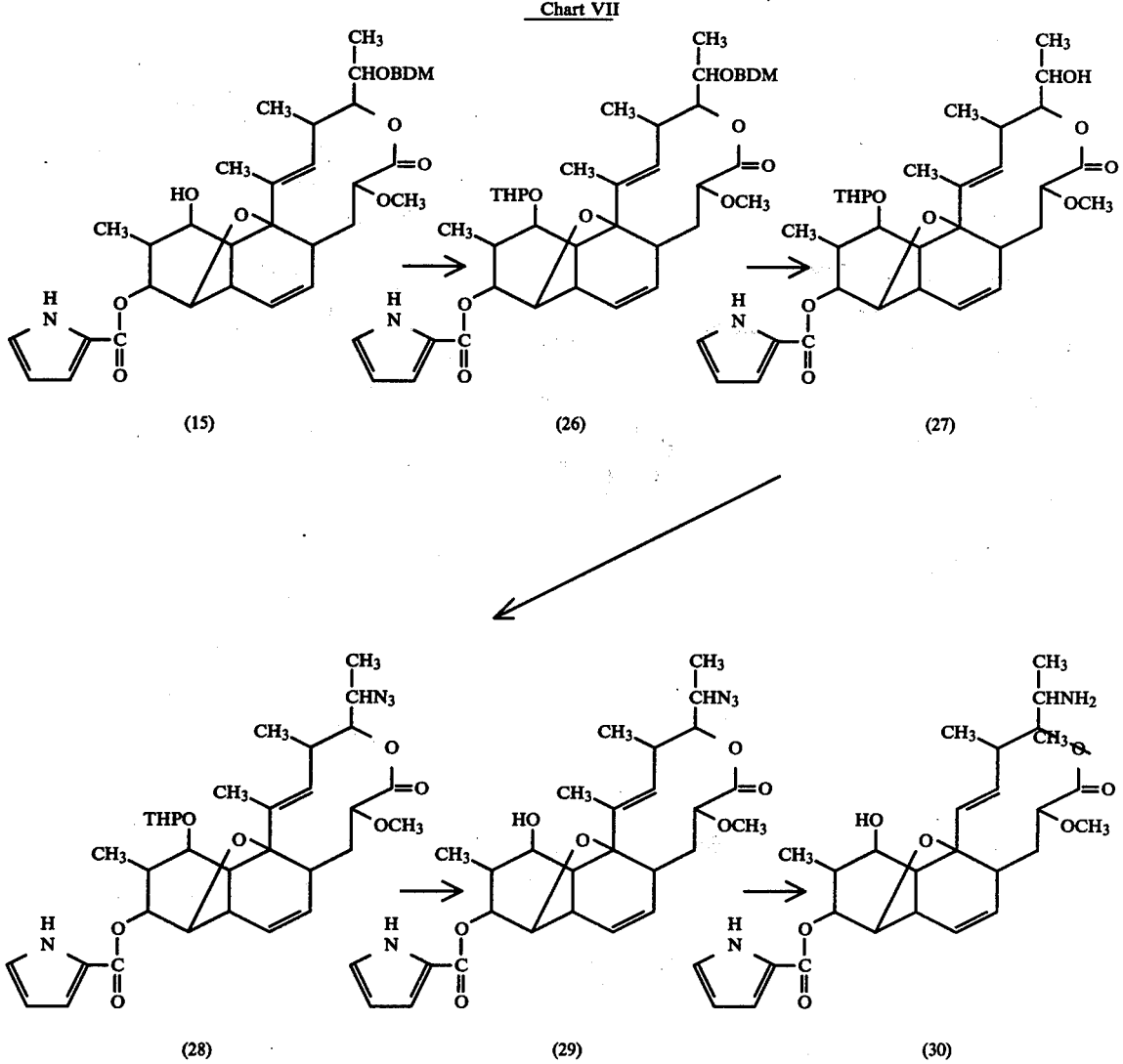
THP =

Chart VIII
Synthesis of Compounds (24) and (25) via Nodusmicin
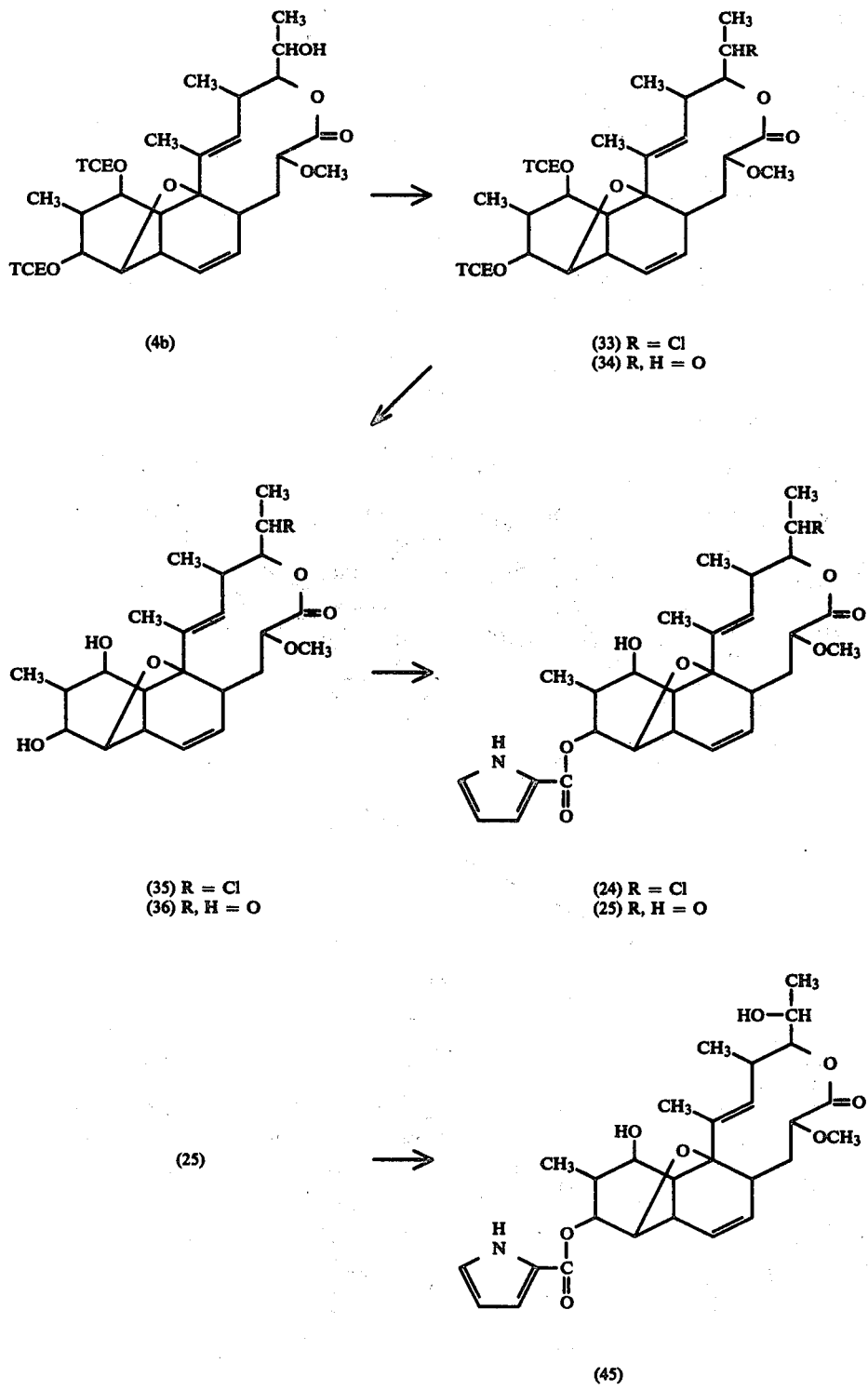
(4b)
(33) R = Cl
(34) R, H = O
(35) R = Cl
(36) R, H = O
(24) R = Cl
(25) R, H = O
(25)
(45)
Compounds 29 and 30 via nodusmicin:

-continued
Chart VIII
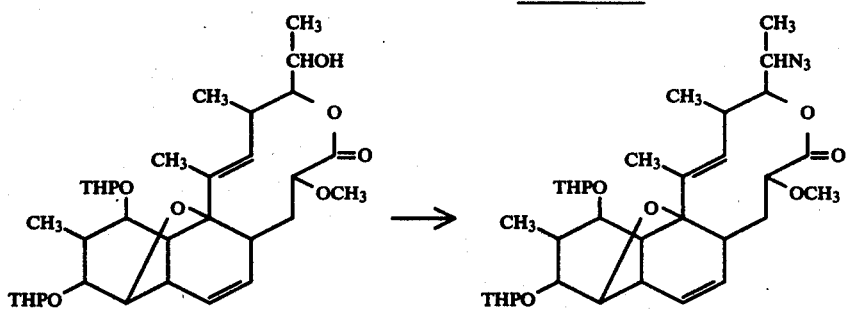
(4c) → (37)
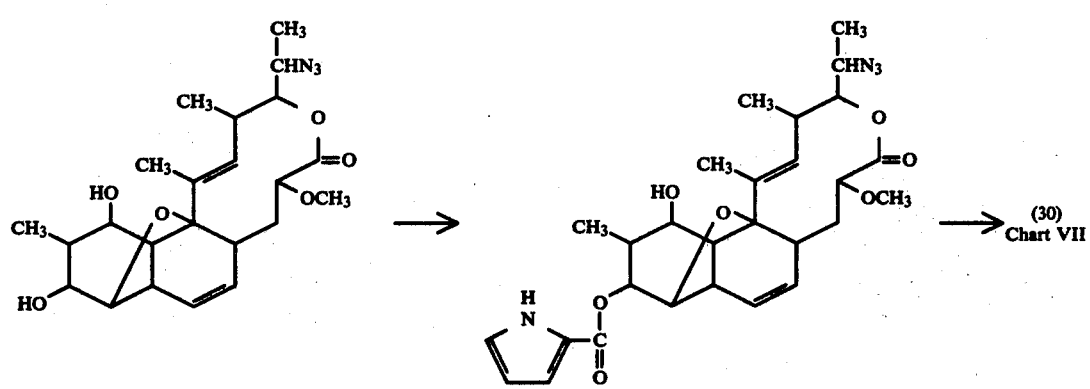
(38) → (29) (Chart VII) → (30) Chart VII
Compounds (20) and (21) via nodusmicin:
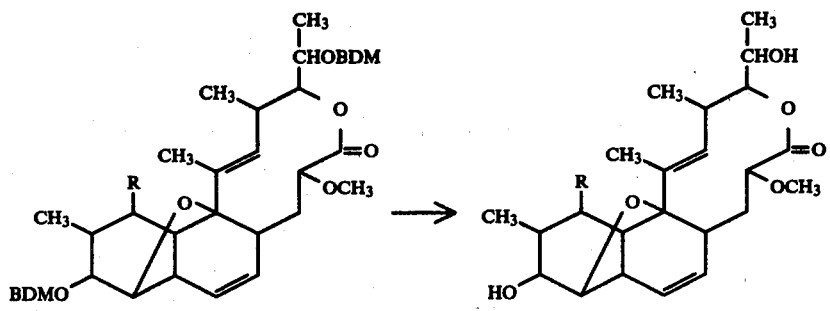
(10a) R = Cl
(10b) R = O
(39) R = Cl
(40) R = O -continued
Chart VIII

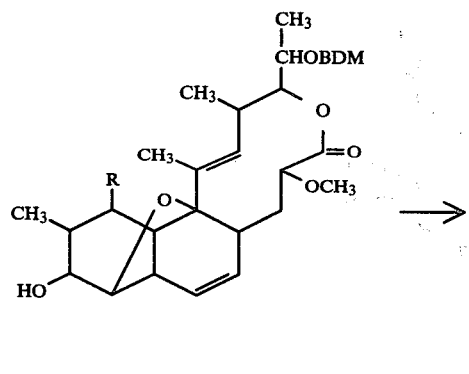

(41) R = Cl
(42) R = O

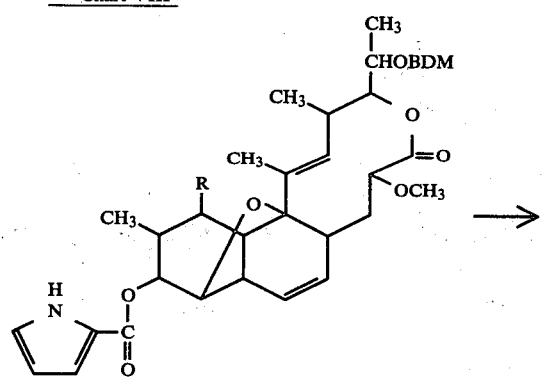

(43) R = Cl
(44) R = O

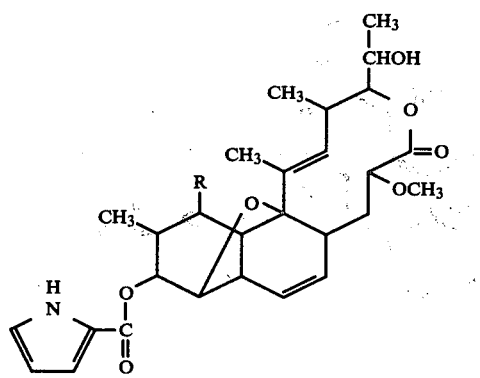

(20) R = Cl
(21) R = O

I claim:
1. A compound of the formula

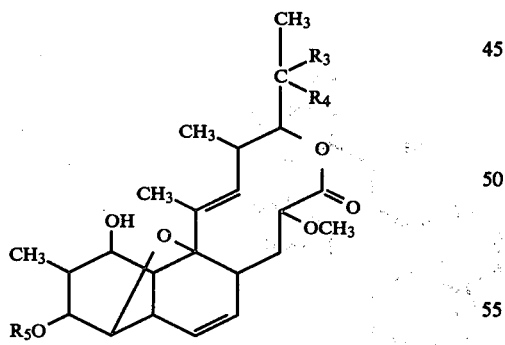

wherein
R₃ and R₄=one is hydrogen and the other is O-arylsulfonyl, wherein aryl can be phenyl or substituted phenyl wherein phenyl can have the substituents p-CH₃ or p-NO₂; O-alkylsulfonyl and substituted O-alkylsulfonyl wherein alkyl is C₁-C₈ inclusive wherein the additional substituent can be CH₃ or CF₃; halogen; azide; amine and substituted amine wherein the substituent can be alkyl of 1 to 3 carbon atoms, inclusive; S alkyl wherein alkyl is C₁-C₈, inclusive; S substituted alkyl wherein the substituent can be —CH₂CH₂OH; nitrile (CN); thio-ester;

wherein alkyl is C₁-C₈, inclusive;

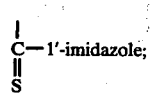

O-alkyl wherein alkyl is C₁-C₈, inclusive;
R₃ and R₄ taken together are =O(ketone); =NOR₈, wherein R₈ is H, alkyl (C₁-C₈, inclusive), alkylidene and substituted alkylidene wherein the substituent can be alkyl of 0-8 carbons, inclusive; =CH—COOC₂H₅; =CHOCH₃;

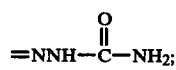

R₃ is OH and R₄ is

wherein R_9 is $(CH_2)_n CH_3$ and n is an integer of from 0–8, inclusive;

R_5 is

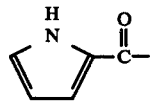

2. A compound, 18-deoxy-18-oxonargenicin $A_1$.

3. A compound, 18-chloro-18-deoxynargenicin $A_1$.

4. A compound, 18-azido-18-deoxynargenicin $A_1$.

5. A compound, 18-O-thiocarbonyl-1'-imidazolenargenicin $A_1$.

6. A compound of the formula

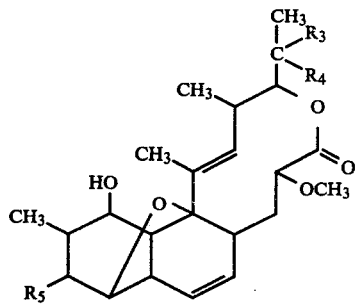

wherein $R_3$ and $R_4$ taken together is =NOH; $R_5$ is pyrrole-2-carbonyl; and the isomers thereof.

7. A compound, according to claim 6, wherein $R_3$ and $R_4$ taken together is =NOCH_3; $R_5$ is pyrrole-2-carbonyl; and the isomers thereof.

8. A compound, according to claim 6, wherein $R_3$ and $R_4$ taken together is

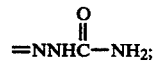

and $R_5$ is pyrrole-2-carbonyl.

* * * * *

UNITED STATES PATENT AND TRADEMARK OFFICE
CERTIFICATE OF CORRECTION

PATENT NO. : 4,448,970

DATED : May 15, 1984

INVENTOR(S) : Barney J. Magerlein

It is certified that error appears in the above-identified patent and that said Letters Patent is hereby corrected as shown below:

Column 1, line 65: "COOH$_2$" should read --COOCH$_2$--.
Column 9, line 63: "5 methylene" should read --5 ml methylene--.
Column 11, lines 38-39: "15.21, 15.1, 15.31" should read --15.21, 15.31--.
Column 13, line 4: "(5H)" should read --(5h)--.
Column 13, line 7: "(5H)" should read --(5h)--.
Column 17, line 56: "104,23," should read --104.23,--.
Column 18, line 8: "128,46," should read --128.46,--.
Column 18, line 44: "81,36," should read --81.36,--.
Column 22, line 12: "Deoxyl-" should read --Deoxy- --.
Column 22, line 22: "134,1," should read --134.1,--.
Column 22, line 42: "82,2," should read --82.2,--.
Column 23 (Chart I, (1) ): should appear as follows:

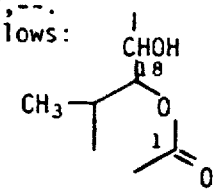

Columns 29 and 30, Chart III (13) and Chart IV (2a): should appear as follows:

Chart III (13)

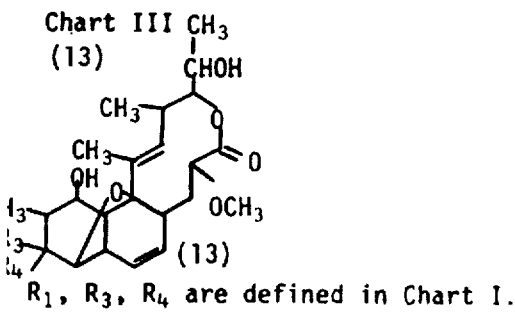

$R_1$, $R_3$, $R_4$ are defined in Chart I.

Chart IV (2a)

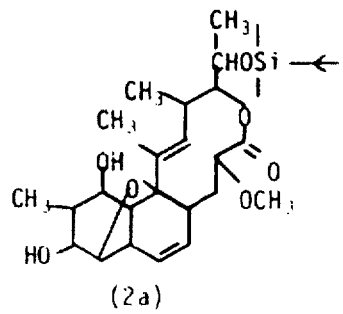

UNITED STATES PATENT AND TRADEMARK OFFICE
CERTIFICATE OF CORRECTION

PATENT NO. : 4,448,970
DATED : May 15, 1984
INVENTOR(S) : Barney J. Magerlein

It is certified that error appears in the above-identified patent and that said Letters Patent is hereby corrected as shown below:

Columns 29-30 (5a): "$\overset{O}{\underset{C-\emptyset}{\|}}$" should read -- $\overset{S}{\underset{C-\emptyset}{\|}}$ --.

Column 29-30 (5d): "$R_2 = COOCH_{CCl3}$" should read -- $R_2 = COOCH_2CCl_3$ --.

Column 34 (30): should read as follows:

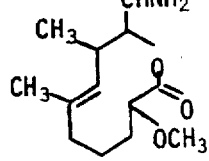

Column 39, lines 66-67: "1 to 3 carbon" should read --1 to 8 carbon--.

Signed and Sealed this

Thirtieth Day of October 1984

[SEAL]

Attest:

Attesting Officer

GERALD J MOSSINGHOFF

Commissioner of Patents and Trademarks